(12) United States Patent
Nagareda et al.

(10) Patent No.: US 10,107,659 B2
(45) Date of Patent: Oct. 23, 2018

(54) SENSOR CLAMP DEVICE, CLAMP-ON ULTRASONIC FLOW METER

(71) Applicant: HONDA ELECTRONICS CO., LTD., Aichi (JP)

(72) Inventors: Kenji Nagareda, Aichi (JP); Yuki Murai, Aichi (JP); Kiyoshi Natsume, Aichi (JP); Yuichi Maida, Aichi (JP)

(73) Assignee: HONDA ELECTRONICS CO., LTD., Aichi (JP)

( * ) Notice: Subject to any disclaimer, the term of this patent is extended or adjusted under 35 U.S.C. 154(b) by 0 days.

(21) Appl. No.: 15/310,223

(22) PCT Filed: Aug. 20, 2015

(86) PCT No.: PCT/JP2015/073314
§ 371 (c)(1),
(2) Date: Nov. 10, 2016

(87) PCT Pub. No.: WO2017/029744
PCT Pub. Date: Feb. 23, 2017

(65) Prior Publication Data
US 2018/0156650 A1 Jun. 7, 2018

(51) Int. Cl.
*G01F 1/66* (2006.01)
*G01F 15/18* (2006.01)
*A61B 8/06* (2006.01)

(52) U.S. Cl.
CPC .............. *G01F 1/662* (2013.01); *A61B 8/06* (2013.01); *G01F 1/667* (2013.01); *G01F 15/18* (2013.01)

(58) Field of Classification Search
CPC ......................................................... G01F 1/66
See application file for complete search history.

(56) References Cited

U.S. PATENT DOCUMENTS

| 4,286,470 A | * | 9/1981 | Lynnworth | ............. | G01F 1/662 |
| | | | | | 73/637 |
| 5,437,194 A | * | 8/1995 | Lynnworth | ............. | G01F 1/662 |
| | | | | | 73/861.27 |

(Continued)

FOREIGN PATENT DOCUMENTS

| JP | 53-027061 | 3/1978 |
| JP | 59-107210 | 6/1984 |

(Continued)

*Primary Examiner* — Harshad R Patel
(74) *Attorney, Agent, or Firm* — Clark & Brody

(57) ABSTRACT

A sensor-clamp device for clamping a pipe of different outer-diameters promptly without having to do a time-consuming sensor-position adjustment includes a pair of ultrasonic-sensors incorporating an ultrasonic-transducer for sending and receiving ultrasonic-waves 'So' and further includes a supporting-plate on which is provided a sliding-mechanism. The pair of ultrasonic-sensors clamps the outer-wall of the pipe in which flows a fluid W1. Of the supporting-plate, the pair of ultrasonic-sensors used in irradiating the ultrasonic-waves 'So' obliquely to the pipe are offset in the axial-line direction of the pipe and firmly placed face to face. The sliding-mechanism slides one of the pair of ultrasonic-sensors obliquely with respect to the axial-line direction of the pipe, thus making the sliding-mechanism to clamp the pipe of various outer-diameters.

9 Claims, 11 Drawing Sheets

(56) References Cited

U.S. PATENT DOCUMENTS

2002/0139198 A1* 10/2002 Ohnishi .................. G01F 1/662
                                                          73/861.27
2004/0123666 A1    7/2004 Ao et al.
2008/0022776 A1*  1/2008 Buchanan ............... G01F 1/662
                                                            73/632
2012/0192656 A1   8/2012 Wiest et al.
2013/0061687 A1   3/2013 Rath et al.
2014/0091675 A1*  4/2014 Nguyen ............... H02N 11/006
                                                           310/300

FOREIGN PATENT DOCUMENTS

JP          4878653        12/2011
JP          4940384         3/2012

* cited by examiner

SENSOR CLAMP DEVICE, CLAMP-ON ULTRASONIC FLOW METER

TECHNICAL FIELD

This invention relates to a sensor-clamp device to be clamped onto a pipe in which fluid flows between a pair of ultrasonic-sensors, and to a clamp-on ultrasonic flow-meter, comprising the sensor-clamp device, for sending and receiving ultrasonic-waves mutually between the pair of ultrasonic-sensors and for calculating, by arithmetic processing, the fluid flow-rate within the pipe according to the time-lag in the propagation of the ultrasonic-waves.

TECHNICAL BACKGROUND

Conventionally, there is a clamp-on ultrasonic flow-meter clamped onto a pipe in which fluid flows and of which the flow-rate is measured from outside the pipe, which is described in e.g. Patent Documents 1 to 3 or the like. Of the above ultrasonic flow-meter, a pair of ultrasonic-sensors is provided thereon by which ultrasonic-waves are obliquely propagated into the fluid flowing within the pipe. The transmission and reception of said ultrasonic-waves is switched between the pair of ultrasonic-sensors for measuring the time lag of said ultrasonic-waves propagating into the fluid, thus calculating the flow-rate of the fluid.

The clamp-on ultrasonic flow-meter, as described in Patent Documents 1 and 2, employs a method for detecting the reflected ultrasonic-waves by providing a pair of ultrasonic-sensors on the same side of the pipe onto which the flow-meter is clamped. The clamp-on ultrasonic flow-meter, as described in Patent Document 3, employs a method for detecting the transparent ultrasonic-waves by providing a pair of ultrasonic-sensors on the opposite side of the pipe onto which the flow-meter is clamped.

PRIOR ARTS

Patent Documents

Patent Document 1: Japanese Patent No. 4878653
Patent Document 2: Japanese Patent No. 4940384
Patent Document 3: Patent Abstracts, Publication No. US 2004/123666

DISCLOSURE OF THE INVENTION

Problems to be Resolved by the Invention

However, the clamp-on ultrasonic flow-meter, as described in Patent Documents 1 and 2, has no adjustment-mechanism for corresponding to the size of the outer-diameter of the pipe. Thus, the measurable-range of the outer-diameter of the pipe is pre-set, so that if the outer-diameter is beyond the measurable-range, a clearance is formed between the pipe and the ultrasonic-sensor, thus causing a defect in the propagation of the ultrasonic waves.

The clamp-on ultrasonic flow-meter, as described in Patent Document 3, has a position-adjustment mechanism for sliding the ultrasonic-sensor laterally in the axial-direction of the pipe. It also has another position-adjustment mechanism that is orthogonally crossed in the thickness-direction of the pipe. This clamp-on ultrasonic flow-meter makes it possible for it to be clamped onto the pipe by the position-adjustment mechanism regardless of variation in the outer-diameter of the pipe, thus making it possible to measure the fluid flow-rate within the pipe. However, the interval in the two directions i.e. the axial-direction and the thickness-direction of the clamp-on ultrasonic flow-meter of Patent Document 3 needs to be adjusted. The optimum position of the ultrasonic-waves in the thickness (longitudinal) direction of the pipe varies according to variation in the outer-diameter of the pipe. The reception-sensitivity of the ultrasonic-waves will be lower if the optimum positional-relationship of the sensor is not kept. To avoid this situation, it is necessary to watch the reception-sensitivity of the ultrasonic-waves and to adjust the position of the ultrasonic-sensor in the thickness (longitudinal) direction of the pipe, which is time-consuming.

This invention was achieved in light of the aforementioned problems in providing a sensor-clamp device that can be promptly clamped onto a pipe of various outer-diameters without a time-consuming sensor-position adjustment and in providing a clamp-on ultrasonic flow-meter to clamp onto the pipe by using the above sensor-clamp device, thus making it possible to measure the fluid flow-rate within the pipe in a short time.

The Means for Resolving the Problems

To solve the aforementioned problems, the first aspect of this invention refers to a sensor-clamp device, characterized in comprising a pair of ultrasonic-sensors incorporating an ultrasonic-transducer for sending and receiving ultrasonic-waves; that it can be clamped in close contact to the outer-wall of a pipe in which fluid is flowing; that it has a supporting-base whereon the pair of ultrasonic-sensors are offset in the axial-direction of the pipe and placed in an opposing manner so that the ultrasonic-waves are obliquely irradiated into the pipe; that it sends and receives such ultrasonic-waves mutually between the pair of ultrasonic-sensors and is used as an ultrasonic flow-meter for calculating by arithmetic processing the flow-rate of the fluid flowing within the pipe according to the ultrasonic-propagation time-lag; and that it has the supporting-base with a sliding-mechanism that can slide at least one of the pair of ultrasonic-sensors obliquely with respect to the axial-direction of the pipe, thus making it possible to clamp a pipe of various outer-diameters.

As such, the first aspect of this invention allows for this basically provided sliding-mechanism to slide at least one of the pair of ultrasonic-sensors obliquely with respect to the axial-direction of the pipe when clamping the sensor-clamp device onto a pipe of various outer-diameters. As such, this sensor-clamp device negates the need for the conventional two-way interval-adjustment in the longitudinal and thickness directions of the pipe, thus making only a one-way sliding adjustment necessary, which makes it possible to clamp a pipe of various outer-diameters promptly without having to do the time-consuming sensor-position adjustment.

The second aspect of this invention refers to a sensor-clamp device, according to the first aspect of this invention, of which the ultrasonic-sensors are slid in the direction in which the ultrasonic-waves are irradiating into the pipe and obliquely forwarding into the fluid flowing within the pipe.

As such, the second aspect of this invention allows for the ultrasonic-sensors to be slid in the direction in which the ultrasonic-waves are irradiating obliquely forward into the fluid flowing within the pipe, thus always retaining the optimum position of each ultrasonic-sensor, thus making it possible in preventing the ultrasonic reception-sensitivity of said ultrasonic-sensors from deteriorating.

The third aspect of this invention refers to a sensor-clamp device, according to the second aspect of this invention, of which the pitch-angle of the ultrasonic-waves forwarding into the fluid flowing within the pipe with respect to the axial-line direction of the pipe is set to be greater than that pitch-angle of the ultrasonic-waves irradiating into the pipe with respect to the axial-line direction of the pipe.

The fluid flowing within the pipe to be measured is preferably a liquid (e.g. water, alcohol, chemical liquid or the like). Generally, the sonic speed of such a liquid is slower than that of the acoustic-propagation agent (e.g. a resin agent). In this case, as described in the above third aspect of this invention, the pitch-angle of the ultrasonic-waves forwarding into the fluid flowing within the pipe, with respect to the axial-line direction of the pipe, is set to be greater than that pitch-angle of the ultrasonic-waves irradiating into the pipe, with respect to the axial-line direction of the pipe. As such, even if the ultrasonic-sensors should slide, the optimum position of each ultrasonic-sensor is surely kept, thus making it possible in preventing the ultrasonic reception-sensitivity of the ultrasonic-sensors from deteriorating.

The fourth aspect of this invention refers to a sensor-clamp device, according to any one of the first to third aspects of this invention, of which the supporting-base comprises a position-adjustment mechanism for adjusting the position of the pipe such that the perpendicular-line passing through the center of the ultrasonic-transducer of the pair of ultrasonic-sensors meets the central-axial line of the pipe.

As such, the fourth aspect of this invention allows for the position-adjustment mechanism to adjust the position of the pipe such that the perpendicular-line passing through the center of the ultrasonic-transducer meets the central-axial line of the pipe. Thus, the propagation-route of the ultrasonic-waves being sent and received between the pair of ultrasonic-sensors runs through the central-axial line of the pipe. In this case, some space corresponding to the outer-diameter of the pipe can be kept as the ultrasonic-propagation-route of the ultrasonic-waves 'So,' thus making it possible to measure the flow-rate of the fluid accurately.

The fifth aspect of this invention refers to a sensor-clamp device, according to the fourth aspect of this invention, of which the position-adjustment mechanism moves up and down by meshing the interval-adjustment work between the pair of ultrasonic-sensors due to the above sliding-mechanism, thus adjusting the position of the pipe.

As such, the fifth aspect of this invention allows for the position-adjustment mechanism to move up and down meshing the interval-adjustment work by the sliding-mechanism, thus adjusting the position of the pipe. Compared to the (conventional) case in that the interval-adjustment work by the sliding-mechanism and the position-adjustment work are done separately, the setting-work of the sensor-clamp device of this invention can be done fairly simply and quickly.

The sixth aspect of this invention refers to a sensor-clamp device, according to any one of the first to the fifth aspects, of which the recommended position of the ultrasonic-sensors as they are being slid and affixed by the sliding-mechanism is defined according to each outer-diameter of the pipe, with a display being provided on the supporting-base of the sensor-clamp device for simultaneously showing that recommended position.

As such, the sixth aspect of this invention allows for the ultrasonic-sensors to slide to the recommended position, as shown on the display, so as to affix the ultrasonic-sensors easily and surely at the suitable position according to the outer-diameter of the pipe, thus making it possible to measure the flow-rate of the fluid accurately.

The seventh aspect of this invention refers to a sensor-clamp device, according to any one of the above first to sixth aspects, of which the sliding-mechanism comprises a guide-trough that obliquely extends on the supporting-base in the direction of the axial-line of the pipe.

As such, the seventh aspect of this invention makes it possible in providing a sliding-mechanism of a comparatively simple design, thus holding down the costs of manufacturing the sensor-clamp device.

The eighth aspect of this invention refers to a sensor-clamp device, according to any one of the above first to seventh aspects, of which the ultrasonic-sensors comprise a plate-like piezoelectric-device as an ultrasonic-transducer; comprise an acoustic-propagation guide with its first-surface contacting the outer-wall of the pipe and its second-surface contacting the piezoelectric-device provided thereon, and being slanted with respect to the first-surface for propagating the ultrasonic waves between the piezoelectric-device and the pipe; and comprise a sensor-holder for holding the acoustic-propagation guide and for attaching it to the supporting-base.

As such, the eighth aspect of this invention allows for the first-surface of the acoustic-propagation guide to make contact with the outer-wall of the pipe, thus providing the plate-like piezoelectric-device on the second-surface that is slanted with respect to the first-surface. By using the acoustic-propagation guide, the ultrasonic-waves generated by the piezoelectric-device can be securely and efficiently irradiated into the pipe at an optimum angle. Also, the ultrasonic-sensor is to be attached to the supporting-base by the sensor-holder, thus making it easy to mount the sensor-clamp device.

The ninth aspect of this invention refers to a clamp-on ultrasonic flow-meter, characterized in comprising a sensor-clamp device, according to any one of the above first to eighth aspects of the invention, and an arithmetic-processing means for calculating the flow-rate of the fluid according to the ultrasonic-propagation time lag.

As such, of the ninth aspect of this invention, the use of the sensor-clamp device allows the one-directional sliding-motion of the sliding-mechanism to clamp the pair of ultrasonic-sensors promptly onto a pipe of various outer-diameters. Thus, in using the clamp-on ultrasonic flow-meter of this invention, it is possible to measure the flow-rate of the fluid in a short time, even if there is a change in the outer-diameter of the pipe.

The tenth aspect of this invention refers to a clamp-on ultrasonic flow-meter, according to the ninth aspect of this invention, of which the arithmetic-processing is the means for automatically detecting the size of the outer-diameter of the pipe according to the ultrasonic-propagation time, thus arithmetically calculating the flow-rate according to the outer-diameter of the pipe.

As such, the tenth aspect of this invention makes it possible to detect automatically the outer-diameter of the various outer-diameters of a pipe, thus efficiently and accurately measuring the flow-rate according to the actual outer-diameter of the pipe.

Effects of the Invention

As described above, the first to eighth aspects of this invention make it possible in providing a sensor-clamp device that promptly clamps onto a pipe of various outer-diameters without doing a time-consuming sensor-position adjustment. Also, the ninth and tenth aspects of this invention make it possible in providing a clamp-on ultrasonic flow-meter that can clamp onto a pipe by using the above sensor-clamp device, thus allowing for measuring the flow-rate of the fluid within the pipe in a short time.

THE FIRST EMBODIMENT

Hereinafter, the first embodiment of this invention embodying the clamp-on ultrasonic flow-meter is described in reference to the drawings.

Figure 1:
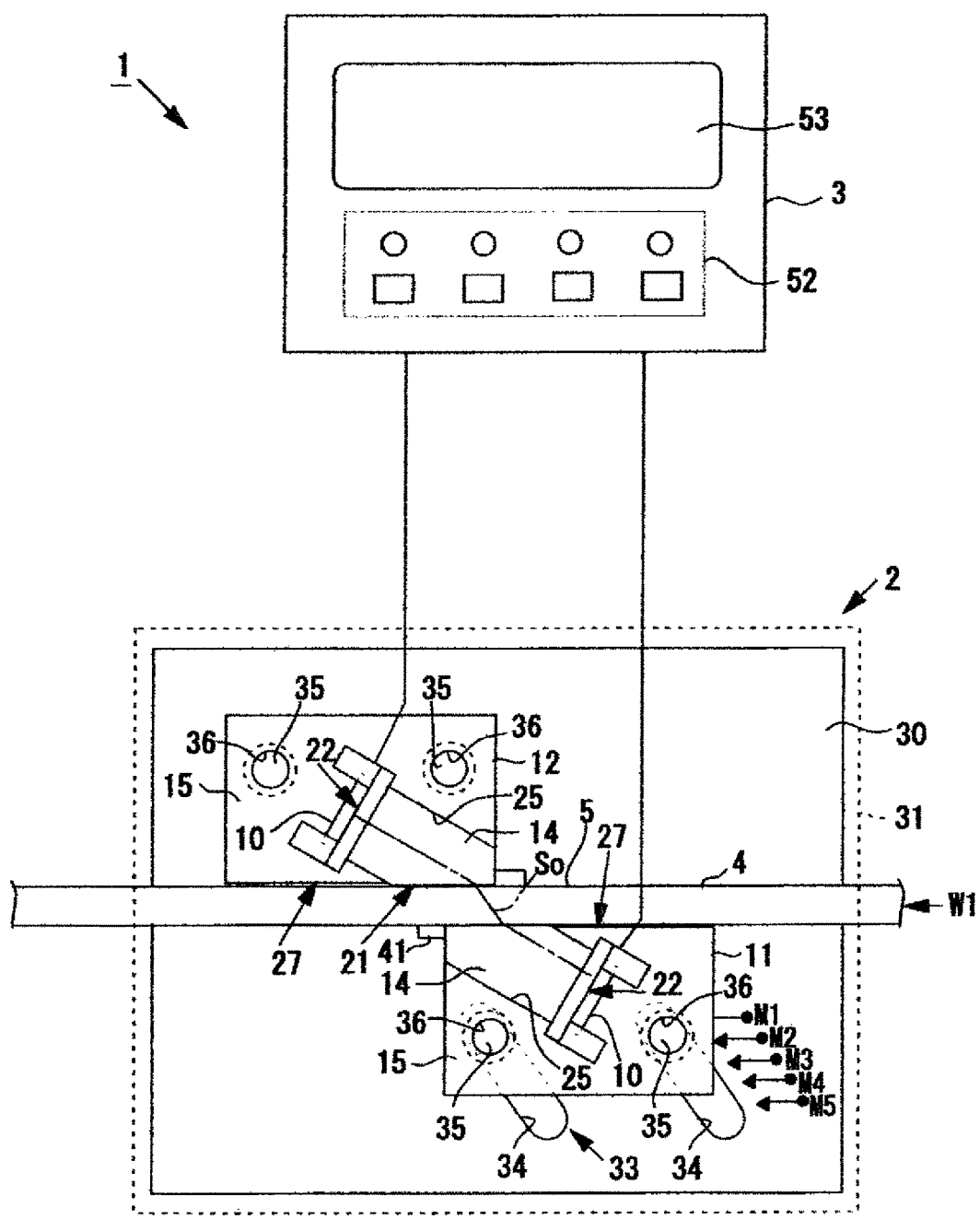
FIG. 1 is the flat view of the clamp-on ultrasonic flow-meter as the first embodiment.

As shown in FIG. 1, the clamp-on ultrasonic flow-meter 1 comprises a sensor-clamp device 2 and a measurement-control device 3 as a flow-rate arithmetic-processing means. The clamp-on ultrasonic flow-meter 1 is a flow-meter for measuring the flow-rate of the fluid W1 (e.g. blood) flowing within the pipe 4 by means of the ultrasonic-propagation time-lag that is used in measuring the flow-rate, for example, during a blood transfusion or the like on the medical front. The sensor-clamp device 2 incorporates a piezoelectric-device 10 as an ultrasonic-transducer that can send and receive ultrasonic-waves 'So' and comprises a pair of ultrasonic-sensors 11, 12 to be clamped in contact to the outer-wall 5 of the pipe 4. The pair of ultrasonic-sensors 11, 12 is arranged on the opposite side of the pipe 4 to detect the ultrasonic-waves (transparent wavelength) passing through the pipe 4. The measurement-control device 3 is electrically connected to each of the ultrasonic-sensors 11, 12 of the sensor-clamp device 2 for arithmetically calculating the flow-rate of the fluid W1 according to the propagation time-lag of the ultrasonic-waves 'So.'

Figure 2:
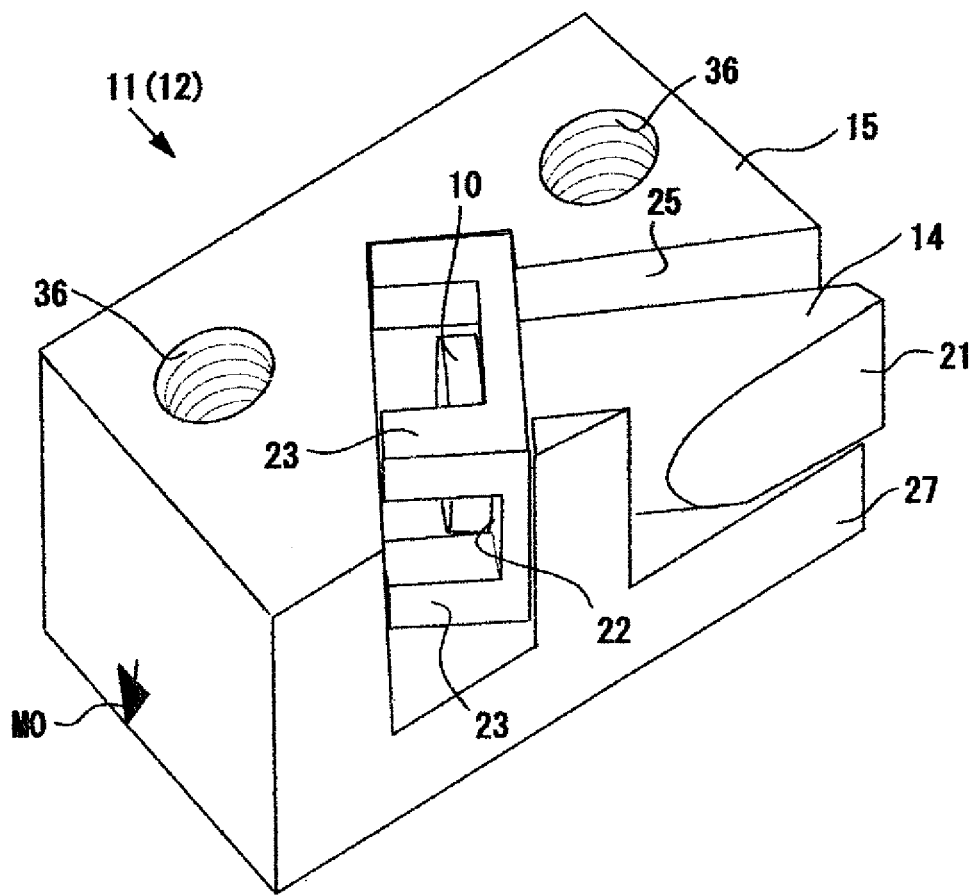
FIG. 2 is the oblique-perspective view of the ultrasonic-sensor as the first embodiment.
Figure 3:
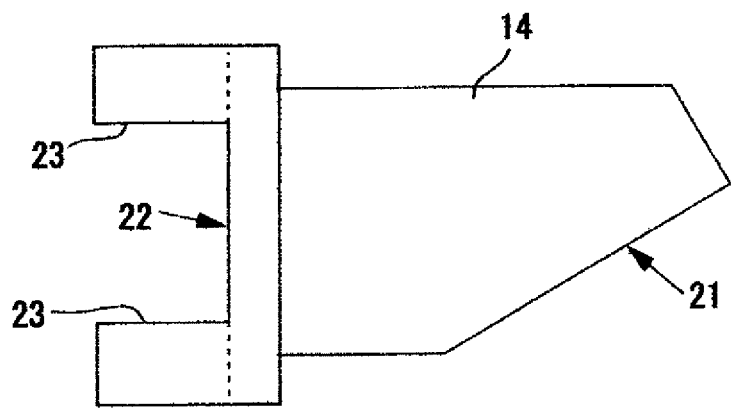
FIG. 3 is the side view of the acoustic-propagation guide.
Figure 4:
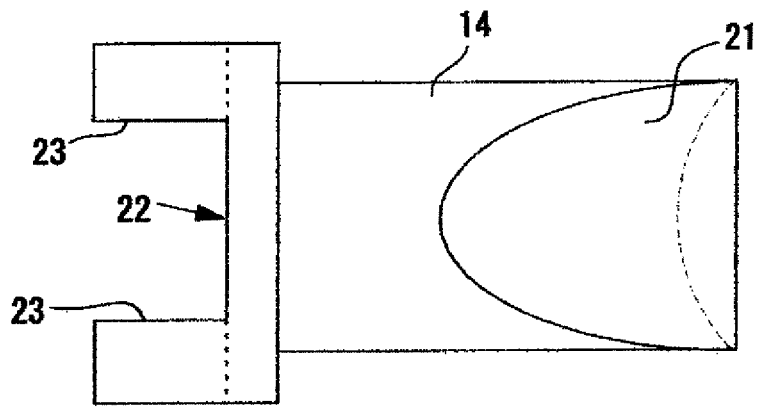
FIG. 4 is the other side view of the acoustic-propagation guide.
Figure 5:
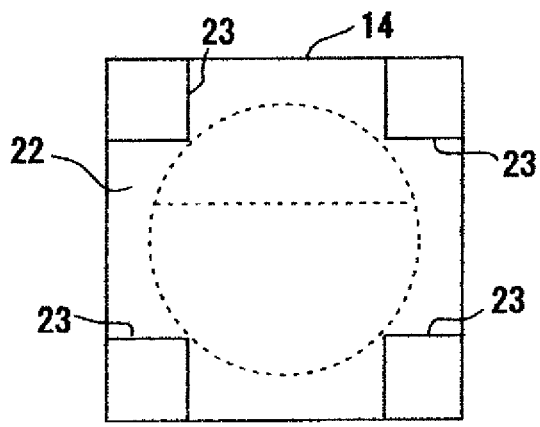
FIG. 5 is the rear view of the acoustic-propagation guide.

Specifically, as shown in FIGS. 1 and 2, the ultrasonic-sensors 11, 12 comprise a disk-like piezoelectric-device 10, an acoustic-propagation guide 14 for propagating the ultrasonic-waves 'So' and a sensor-holder 15 for holding the acoustic-propagation guide 14. The pair of ultrasonic-sensors 11, 12 have mutually the same structure. The piezoelectric-device 10 is formed by piezoelectric ceramics such as e.g. PZT or the like.

As shown in FIGS. 2 to 5, the acoustic-propagation guide 14 that is formed e.g. by resin ingredients into a nearly cylindrical shape has a contact-surface 21 (first-surface) contacting the outer-wall 5 of the pipe 4 and a mounting-surface 22 (second-surface) that is slanted with respect to the contact-surface 21. Also provided is the piezoelectric-device 10. The contact-surface 21 of the pipe 4 is provided at the tip of the acoustic-propagation guide 14, and the mounting-surface 22 of the piezoelectric-device 10 is provided at the base of the acoustic-propagation guide 14, thus allowing for the ultrasonic-waves 'So' to propagate between the piezoelectric-device 10 of the mounting-surface 22 and the pipe 4 of the contact-surface 21. Specifically, the contact-surface 21 is formed obliquely as the cutting-part at the tip of the cylindrical-shaped acoustic-propagation guide 14. Also, the base of the acoustic-propagation guide 14, whereat the mounting-surface 22 is provided, is shaped like a square. A supporting-column 23 is provided protruding from each of the four corners of the mounting-surface 22 of the piezoelectric-device 10 to protect the piezoelectric-device 10 itself. Thus, the piezoelectric-device 10 is arranged within the four supporting columns 23.

As shown in FIGS. 1 and 2, the sensor-holder 15 of the embodiment of this invention is formed as a square box of a resin material. The sensor-holder 15 has a concave-section 25 in which is placed the acoustic-propagation guide 14 to which the piezoelectric-device 10 is attached. Of the sensor-holder 15, the concave-section 25 is partially open to the surface 27. Of the acoustic-propagation guide 14, upon being placed into the concave-section 25 of the sensor-holder 15, the contact-surface 21 (first-surface) of said acoustic-propagation guide 14 is parallel to the surface 27 of the sensor-holder 15, and such acoustic-propagation guide 14 is arranged so that the contact-surface 21 is slightly projected beyond the surface 27 of the sensor-holder 15. Of the sensor-clamp device 2, the pipe 4 is arranged along the surface 27 of the sensor-holder 15, which is parallel to the contact-surface 21 of the acoustic-propagation guide 14. Of this embodiment, the pipe 4 is a transfusion-tube made of a flexible resin material and has an outer-diameter of 2 to 10 mm.

Figure 6:
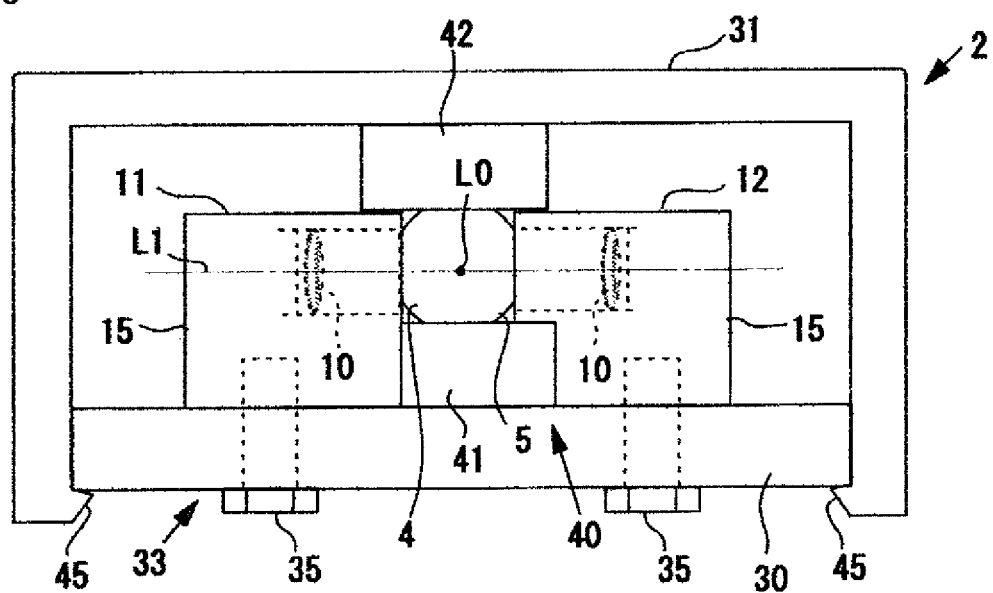
FIG. 6 is the side view of the sensor-clamp device as the first embodiment.

As shown in FIGS. 1 and 6, the sensor-clamp device 2 of the embodiment of this invention comprises the pair of ultrasonic-sensors 11, 12 and a supporting-plate 30 (supporting-base) for supporting the pair of ultrasonic-sensors 11, 12 and the cross-sectional U-shaped cover-part 31 for covering each of the ultrasonic sensors 11, 12. Of the supporting-plate 30, the pair of ultrasonic-sensors 11, 12 for irradiating the ultrasonic-waves 'So' obliquely into the pipe 4 are offset on the upper and lower sides of said supporting-plate 30 in the axial-line direction of the pipe 4 and then firmly placed face to face.

The supporting-plate 30 has a sliding-mechanism 33 for obliquely sliding the sensor 11 out of its paired position with the sensor 12 with respect to the axial-line direction of the pipe 4. The sliding-mechanism 33 of the embodiment of this invention comprises two guide-troughs 34 extending obliquely with respect to the axial-line direction of the pipe 4 and comprises two affixing-bolts 35 for affixing each guide-trough 34 to the ultrasonic-sensor 11. Of this embodiment, the through-holes 36 (see FIG. 2) into which the affixing-bolts 35 are to be inserted are vertically provided within the sensor-holder 15 of the ultrasonic-sensor 11. The affixing-bolts 35 are inserted into the through-holes 36, thereby affixing the ultrasonic-sensor 12 onto the supporting-plate 30.

Figure 7:
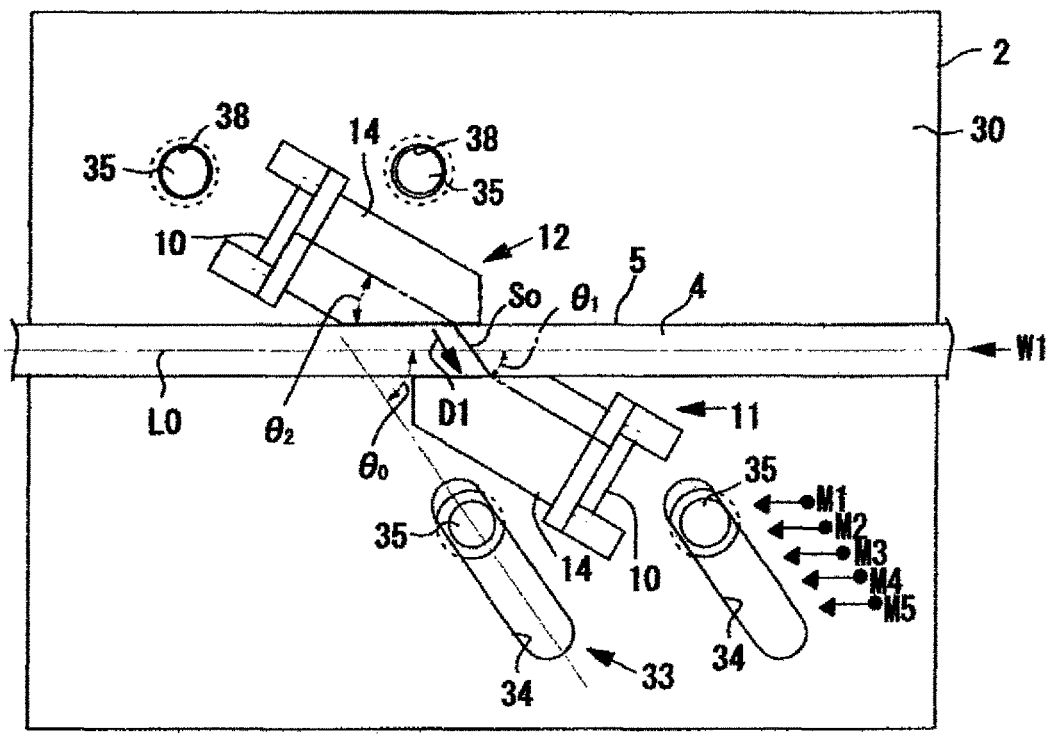
FIG. 7 is the explanatory diagram showing the pitch-angle of the ultrasonic-waves forwarding into the acoustic-propagation guide and into the pipe with respect to the axial-line direction of the pipe.

Each guide-trough 34 is provided in parallel to the direction in which the ultrasonic-waves 'So' are irradiated obliquely forward into the pipe 4 in which the fluid W1 is flowing within the pipe 4. In other words, as shown in FIG. 7, in the case that the axial-line direction of the pipe 4 is specified as being the base, the pitch-angle $\theta_0$ of the guide-trough 34 is equal to the angle $\theta_1$ that indicates the direction D1 of the ultrasonic waves 'So' forwarding into the fluid W1. ($\theta_0 = \theta_1$) For the purpose of illustration, FIG. 7 shows each of the ultrasonic-sensors 11, 12 without the sensor-holder 15. As such, of the sliding-mechanism 33 of the embodiment of this invention, each guide-trough 34 is provided such that the ultrasonic-sensor 11 is to be slid in the direction D1 in which the ultrasonic-waves 'So' are obliquely forwarding into the fluid W1.

Of the pair of ultrasonic-sensors 11, 12 the ultrasonic-sensor 12 is provided on the opposite side of the sliding-mechanism 33 and is immovably affixed onto the supporting-plate 30. Specifically, two through-holes 36, into which the ultrasonic-sensor 12 is affixed, are formed in the supporting-plate 30, and an affixing-bolt 35 is inserted into each through-hole 36 (see FIG. 5 or the like) of the sensor-holder 15, thus immovably affixing the ultrasonic-sensor 12 onto the supporting-plate 30.

An ultrasonic-sensor 11, according to the outer-diameter of the pipe 4, is slid to a specified position on the guide-trough 34 and affixed thereat by an affixing-bolt 35. As a result, the interval between the pair of ultrasonic-sensors 11, 12 on the sensor-clamp device 2 is adjusted according to the diameter of the pipe 4, thus allowing for the pair of ultrasonic-sensors 11, 12 to be clamped onto said pipe 4 of various outer-diameters.

Of the sensor-clamp device 2 of the embodiment of this invention, the pitch-angle $\theta_1$ of the ultrasonic-waves 'So' forwarding into the fluid W1 within the pipe 4 with respect to the axial-line direction of said pipe 4 is set to be greater than the pitch-angle $\theta_2$ of the ultrasonic-waves 'So' upon irradiating into said pipe 4 with respect to the axial-line direction (i.e. $\theta_1 > \theta_2$). The pitch-angle $\theta_2$, upon the ultrasonic-waves 'So' irradiating into the pipe 4, is the angle that shows the moving-direction of the ultrasonic waves 'So' on the acoustic-propagation guide 14, which is equal to the pitch-angle of the disk-like piezoelectric-device 10 with respect to the axial-line direction of said pipe 4 (i.e. the angle of the normal vector of the piezoelectric-device 10).

Figure 8:
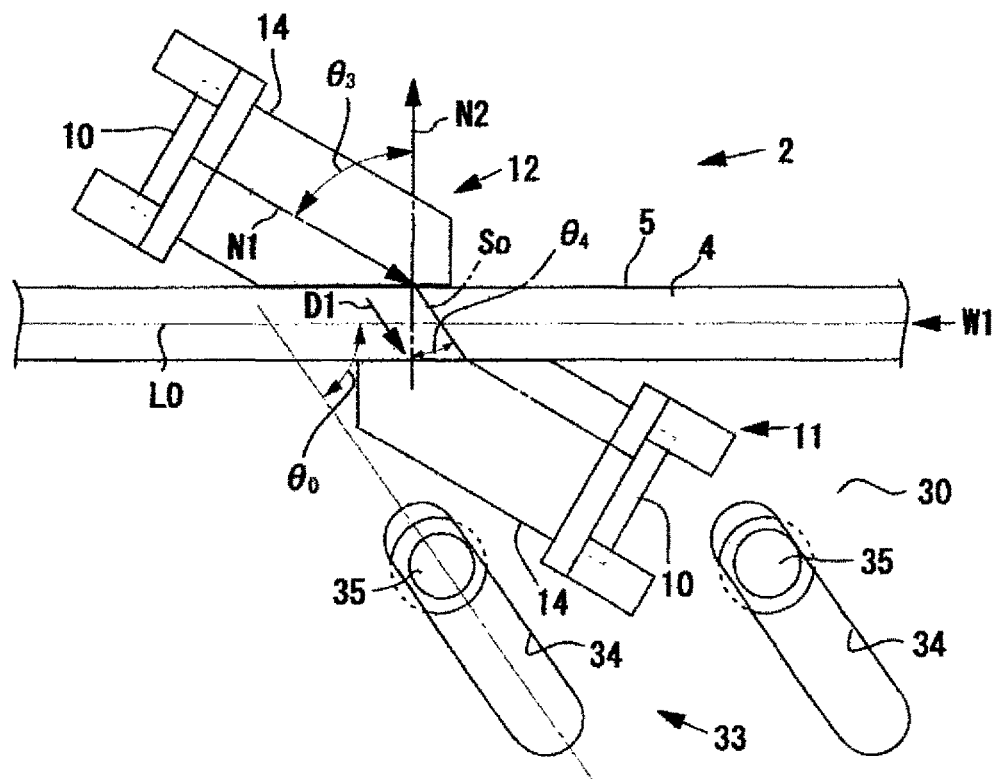
FIG. 8 is the explanatory diagram showing the pitch-angle of the guide-trough with respect to the axial-line direction of the pipe.

As shown in FIG. 8, on the condition that the crossing-angle between the normal-vector N1 of the piezoelectric-device 10 and the normal-vector N2 of the flow-path within the pipe 4 is specified as $\theta_3$ [rad], the sonic-speed to propagate the acoustic-propagation guide 14 is specified as $c_1$, and the sonic-speed within the fluid W1 is specified as $c_2$. The incident-angle $\theta_4$ [rad] within the pipe 4 should be as shown below.

[Formula 1]

$$\theta_4 = \arcsin\left(\frac{\sin\theta_3}{c_1} \times c_2\right) \tag{1}$$

As shown in FIG. 8, of the embodiment of this invention, the crossing-angle $\theta_3$ is set at 60°. The propagating sonic-speed $c_1$ of the acoustic-propagation guide 14 is set at e.g. 2,200 m/s. The sonic-speed $c_2$ of the fluid W1 (e.g. blood) is set at e.g. 1,600 m/s. In this case, the incident-angle $\theta_4$ of the ultrasonic-waves 'So' within the pipe 4 is 39°. The sonic-speed within the wall of the pipe 4 is equal to the sonic-speed $c_2$ of the fluid, and the incident-angle of the ultrasonic-waves 'So' within the pipe-wall is the angle $\theta_4$, which is the same as that of the ultrasonic-waves 'So' in the fluid W1. Therefore, the wall of the pipe 4 is omitted in FIG. 8.

As shown in FIG. 8, if the crossing-angle $\theta_3$ is described by the pitch-angle $\theta_2$ with respect to the axial-line direction of the pipe 4, as shown in FIG. 7, its formula will be $\theta_3 = 90° - \theta_2$. Also, as shown in FIG. 8, the incident-angle $\theta_4$ of the ultrasonic-waves 'So' within the pipe 4 is described by the pitch-angle $\theta_1$ with respect to the axial-line direction of the pipe 4, as shown in FIG. 7. Its formula will be $\theta_4 = 90° - \theta_1$. The guide-trough 34 of the embodiment of this invention is formed with the pitch-angle $\theta_0$, which is the same as the incident-angle $\theta_4$ of 39° of the ultrasonic-waves 'So' within the pipe 4 (the same as the pitch-angle $\theta_1$ of 51° with respect to the axial-line direction of the pipe 4 when the ultrasonic-waves 'So' are forwarding through the fluid W1).

Figure 9:
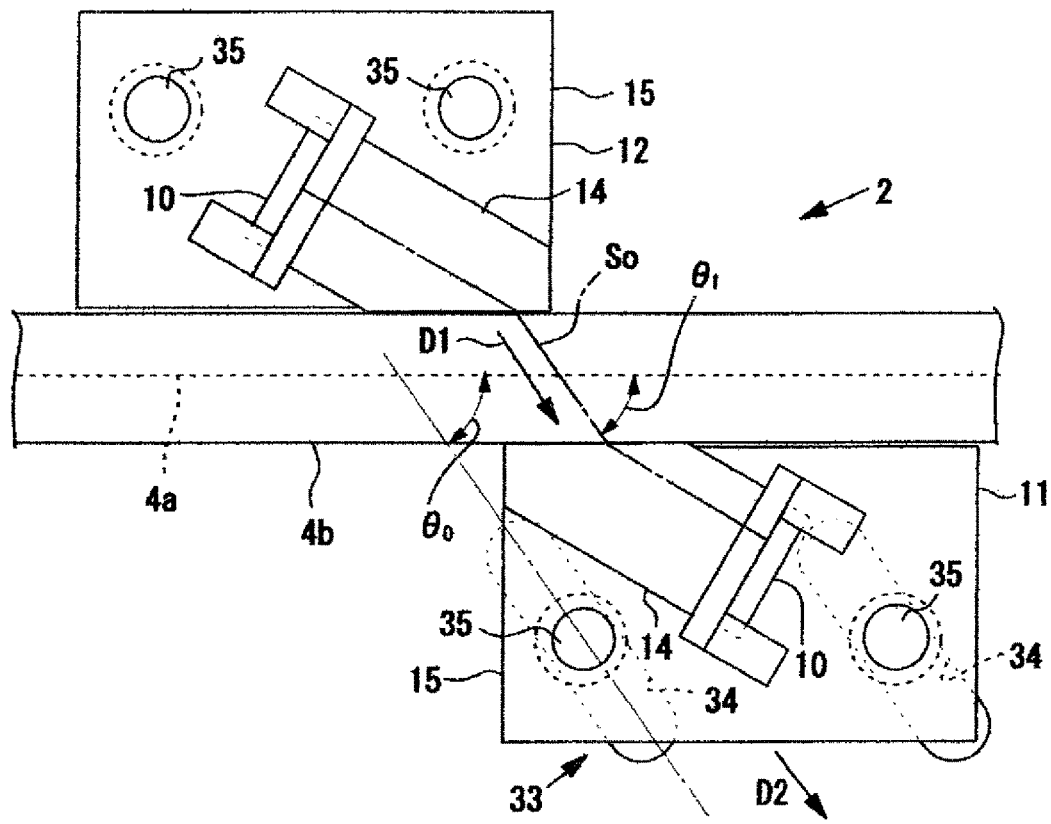
FIG. 9 is the explanatory diagram showing the sliding-direction of the ultrasonic-sensors.

As shown in FIG. 9, regarding the sensor-clamp device 2 having the guide-trough 34 formed with such a pitch-angle $\theta_0$, in the case e.g. in which the pipe 4a of a small outer-diameter is changed to the pipe 4b of a larger outer-diameter, the ultrasonic-sensor 11 is slid obliquely along to the guide-trough 34. In this case, the sliding-direction D2 of the ultrasonic-sensor 11 is identical to the sliding-direction D1 in which the ultrasonic-waves 'So' are forwarding within the pipe 4 of the larger outer-diameter. In other words, resizing the pipe 4b elongates the propagation-pathway of the ultrasonic-waves 'So' within the pipe 4. Then, the ultrasonic-sensor 11 is slid to such an elongated-distance extending along the propagation-pathway. As such, the sensor-clamp device 2 of the embodiment of this invention allows for the sliding-mechanism 33 to slide the ultrasonic-sensor 11, thus controlling the deterioration of the reception-sensitivity of the ultrasonic-waves 'So' between the ultrasonic-sensors 11, 12.

It is possible to set the pitch-angle $\theta_0$ of the guide-trough 34 within the range of ±10° with respect to the angular-direction of the pitch-angle $\theta_1$, so that the sliding-mechanism 33 is formed to slide the ultrasonic-sensor 11 at the angle of ±10° with respect to the direction D1 in which the ultrasonic-waves 'So' are forwarding in the fluid W1.

The sensor-clamp device 2 of the embodiment allows for the sliding-mechanism 33 to specify per each outer-diameter the recommended position of the pipe 4 when sliding the ultrasonic-sensor 11 and then affixing it. The display showing the recommended position per each outer-diameter is provided in the vicinity of the guide-trough 34 of the supporting-plate 30. Specifically, the indicator, e.g. the model number of the pipe 4 and the recommended positions according to the outer-diameters such as M1, M2, M3, M4 or M5 are printed on the surface of the supporting-plate 30 (see FIGS. 1 and 7). On the other hand, the reference mark M0 showing the reference-position for adjusting the position of the ultrasonic-sensor 11 is printed on the surface of the sensor-holder 15 of the ultrasonic-sensor 11 (see FIG. 2). The sliding-mechanism 33 allows for the ultrasonic-sensor 11 to be slid until the reference mark M0 on the side of the sensor-holder 15 corresponds to the recommended positions M1 to M5 according to the outer-diameters of the pipe 4, and then affixing the ultrasonic-sensor 11 by the affixing-bolt 35. Thus, the suitable distance according to the outer-diameter of the pipe 4 is ensured between the pair of ultrasonic-sensors 11, 12 so that the pipe 4 is firmly clamped. In this case, the length of the propagation-route of the ultrasonic-waves 'So' is specific according to the outer-diameter, thus making it possible to control any error in the flow-rate measurement.

As shown in FIG. 6, the sensor-clamp device 2 of the embodiment has a position-adjustment mechanism 40 for adjusting the position of the pipe 4 by supporting the pipe 4 from both sides in the orthogonal-direction in which the pair of the ultrasonic-sensors 11, 12 are placed face-to-face (vertically as shown in FIG. 6). Specifically, a pressing-member 41 (an elastic body such as e.g. a sponge or the like) is arranged beneath the pipe 4 and against the upper-surface of the supporting plate 30. The pressing-member 42 (an elastic body such as e.g. a sponge or the like) is arranged above the pipe 4 and against the inner-wall of the U-shaped cover-part 31.

On the supporting-plate 30, the pressing-member 41 is arranged between the sensor-holders 15 of the ultrasonic-sensors 11, 12. When adjusting the interval between the ultrasonic-sensors 11, 12 by sliding the ultrasonic-sensor 11 through the sliding-mechanism 33, the thickness of the pressing-member 41 is changed by the suppressed strength of the sensor-holder 15. Specifically, the pressing-member 41 becomes thicker as the interval between the ultrasonic-sensors 11, 12 narrows. Contrarily, the pressing-member 41 becomes thinner as the interval between the ultrasonic-sensors 11, 12 widens. In this embodiment, the vertical position of the pipe 4 is adjusted such that the perpendicular-line L1 crossing the center of the piezoelectric-devices 10 on the pair of the ultrasonic-sensors 11, 12 crosses the central axial-line L0 of the pipe 4 according to the variation in thickness of the pressing-member 41.

A hook 45 is formed at the bottom of the as-seen cross-sectional U-shaped cover 31. A hook 45 is latched to each end of the supporting-plate 30, thereby firmly attaching the U-shaped cover-part 31 and thus covering the ultrasonic-sensors 11, 12. With the U-shaped cover 31 attached, the pressing-member 42 that is arranged above the pipe 4 and against the inner-wall of the cover 31 presses the pipe 4 from above. Consequently, the pressing-members 41, 42 press the pipe 4 upward and downward, thus firmly affixing the pipe 4 so as not to come off vertically.

Figure 10:
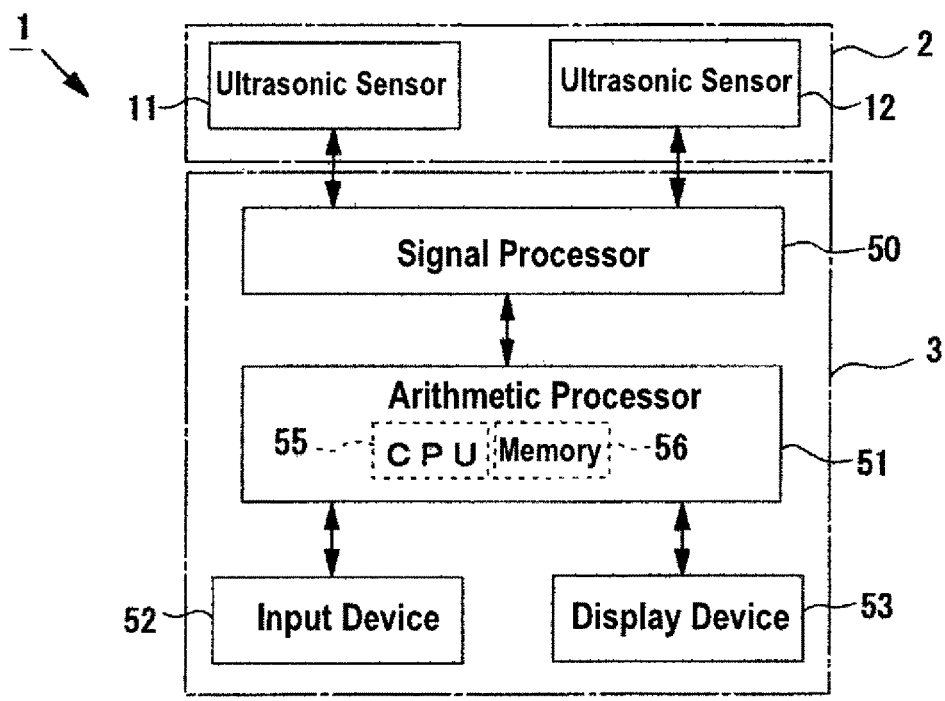
FIG. 10 is the block diagram showing the electrical structure of the clamp-on ultrasonic flow-meter.

As shown in FIG. 10, the measurement-control device 3 comprises a signal-processor 50, an arithmetic-processor 51, an input-device 52 and a display-device 53 or the like. The signal-processor 50 has a circuit for emitting the drive-signal that activates each of the ultrasonic-sensors 11, 12 and has another circuit for detecting the propagation-time of the ultrasonic-waves 'So' or the like. The arithmetic-processor 51 is a processing-circuit comprising the conventional and widely known CPU55 and memory 56 or the like. A control-program or data is stored in the memory 56 of the arithmetic-processor 51, and the CPU55 arithmetically processes the flow-rate according to the control-program in the memory 56 and then displays it.

Specifically, the signal-processor 50 activates each of the ultrasonic sensors 11, 12 to send and receive the ultrasonic waves 'So' mutually at which time the signal-processor 50 detects the propagation-time of the ultrasonic-waves 'So' propagating in the positive-direction (that is, the propagation-time of the ultrasonic-waves 'So' propagating in the positive-direction with respect to the flow of the fluid W1) that is being sent from the ultrasonic-sensor 11 on the upper-side and being received by the ultrasonic-sensor 12 on the lower-side. At this time, the signal-processor 50 detects the propagation-time of the ultrasonic-waves 'So' propagating in the negative-direction (that is, the propagation-time of the ultrasonic-waves 'So' propagating in the negative-direction with respect to the flow of the fluid W1) that is being sent from the ultrasonic-sensor 12 on the lower-side and being received by the ultrasonic-sensor 11 on the upper-side. The signal-processor 50 then emits the positive-negative-direction propagation-time to the arithmetic-processor 51 for it to be read by it. Thus, the flow-rate of the fluid W1 is arithmetically calculated according to such propagation times.

The input-device 52, having various operational buttons, sets the starting and ending of the measurement and sets the display mode. The display-device 53 is e.g. a crystal-liquid display that shows the flow-rate being calculated by the arithmetic-processor 51.

Regarding the clamp-on ultrasonic flow-meter 1 of the embodiment of this invention, the measurement-control device 3 has functions for automatically detecting the outer-diameter of the pipe 4 to be clamped by the sensor-clamp device 2 and for calculating the appropriate flow-rate according to that outer-diameter. Hereinafter, the method for calculating the flow-rate by the clamp-on ultrasonic flow-meter 1 of the embodiment is described.

Firstly, the method for detecting the outer-diameter of the pipe 4 by the propagation-time of the ultrasonic-waves 'So' is described. The arrival-time of the ultrasonic-waves 'So' propagating between the pair of ultrasonic-sensors 11, 12 includes the propagation-time in the flow-path of the pipe 4 and of that within the wall of the acoustic-propagation guide 14 and the pipe 4 and the delay time in the electrical circuit. In the embodiment of this invention, the pipe 4 is initially totally pressed down to measure the ultrasonic-waves 'So' on the condition that there be no flow-path between the ultrasonic-sensors 11, 12. Thus, this initial setting should be zero-point propagation-time to, which is stored in the memory 56 of the arithmetic-processor 51 of the measurement-control device 3.

Next, an ultrasonic-sensor 11 is firmly affixed at the recommended position according to the outer-diameter of the pipe 4, so as to slip the pipe in between the pair of ultrasonic-sensors 11, 12, thus setting the sensor-clamp device 2 for measuring the flow-rate. As such, the ultrasonic-waves 'So' are sent and received between the pair of ultrasonic-sensors 11, 12 of the sensor-clamp device 2. At this time, the arithmetic-processor 51 of the measurement-control device 3 arithmetically calculates the time at by deducting the zero-point propagation-time to from the propagation-time t being measured by the signal-processor 50 using the following formula (2) and then identifying such time Δt as the propagation-time within the flow-path and then storing it in the memory 56.

Formula (2)

$$\Delta t = t - t_0 \quad (2)$$

After calculating the propagation-time $t_1$ of the ultrasonic-waves 'So' in the positive-direction in which they are being sent from the ultrasonic-sensor 11 on the upper-side and being received by the ultrasonic-sensor 12 on the lower-side, and after calculating the propagation time $t_2$ of the ultrasonic-waves 'So' in the negative-direction in which they are being sent from the ultrasonic-sensor 12 on the lower-side and being received by the ultrasonic-sensor 11 on the upper-side, the average value of $((t_1+t_2)/2)$ as the propagation-time t can then be specified.

The arithmetic-processor 51 calculates the surface-separation d of the flow-path by the following formula (3) together with the propagation-time Δt within the flow-path and calculates the sonic-speed $c_2$ within the fluid W1 and the incident-angle $\theta_4$ of the ultrasonic-waves 'So' within the flow-path.

Formula (3)

$$d = c_2 \times \Delta t \times \cos \theta_4 \quad (3)$$

The arithmetic-processor 51 determines the type of pipe 4 to be clamped by the sensor-clamp device 2 according to the surface-separation d calculated by the above formula (3) and then automatically detects the outer-diameter of said pipe 4. The arithmetic processor 51, using the surface-separation d, detects the information of the measurement-environment such as the distance between the ultrasonic-sensors 11, 12 and the length of the propagation-pathway of the ultrasonic-waves 'So' and the cross-sectional area of the flow-path or the like.

Hereinafter, the arithmetic processing for measuring the flow-rate is described.

The arithmetic-processor 51 subtracts the zero-point propagation-time to from the propagation-times $t_1$ and $t_2$ in the positive and negative directions respectively that have been measured by the signal-processor 50 and then calculates the propagation-times $\Delta t_1$ and $\Delta t_2$ in the positive and negative directions respectively within the flow-path, thus arithmetically calculating the flow-speed V within the fluid W1 by the following formula (4) using the propagation-times $\Delta t_1$, $\Delta t_2$ and the surface-separation d within the flow-path calculated by the formula (3) and the incident-angle $\theta_4$ of the ultrasonic-waves 'So' within the flow-path.

Formula (4)

$$V = \frac{d}{(2 \times \sin\theta_4 \times \cos\theta_4)} \times \left(\frac{1}{\Delta t_1} - \frac{1}{\Delta t_2}\right) \quad (4)$$

Then, the arithmetic-processor 51 arithmetically calculates the volume flow-rate Q of the fluid W1 by the following formula (5) and by using the cross-sectional area A of the flow-path as determined by the surface-separation d and the flow-speed V of the fluid W1.

Formula (5)

$$Q = S \times V \quad (5)$$

The arithmetic-processor 51 sends the arithmetic-value data of the volume flow-rate Q to the display-device 53. Based on that data, the volume flow-rate of the fluid W1 is displayed. As such, in using the clamp-on ultrasonic flow-meter 1 of the embodiment of this invention, the volume flow-rate Q of the fluid W1 flowing within the pipe 4 is measured.

Therefore, the embodiment of this invention realizes the following effects.

(1) The sensor-clamp device 2 of the embodiment of this invention has the sliding-mechanism 33 for sliding the ultrasonic-sensor 11 obliquely in the axial-line direction of the pipe 4. Providing this sliding-mechanism 33 negates the conventional two-way interval-adjustment in the longitudinal and thickness directions of the pipe 4, thus making only a one-way (oblique-direction D2) sliding-adjustment necessary, which makes it possible in clamping the pipe 4 of various outer-diameters promptly without having to do a time-consuming sensor-position adjustment.

(2) The sensor-clamp device 2 of the embodiment of this invention allows for the ultrasonic-sensor 11 to be slid in the direction D1 in which the ultrasonic-waves 'So' are being irradiated obliquely forward into the fluid W1 flowing within the pipe 4, thus always retaining the optimum position of each of the ultrasonic-sensors 11, 12 and thus making it possible in preventing the reception-sensitivity of the ultrasonic-waves 'So' of the ultrasonic-sensors 11, 12 from deteriorating.

(3) Regarding the sensor-clamp device 2 of the embodiment of this invention, the pitch-angle $\theta_1$ of the ultrasonic-waves 'So' forwarding into the fluid W1 flowing within the pipe 4 with respect to the axial-line direction of the pipe 4 is set to be greater than that $\theta_2$ of the ultrasonic-waves 'So' with respect to the axial-line direction of the pipe 4, as the ultrasonic-waves 'So' are irradiating into the pipe 4 (see FIG. 7). Thus, even if the ultrasonic sensor 11 should slide, the optimum position of each of the ultrasonic sensors 11, 12 is surely kept, thus making it possible in preventing the reception-sensitivity of the ultrasonic-waves 'So' of the ultrasonic sensors 11, 12 from deteriorating.

(4) Regarding the sensor-clamp device 2 of the embodiment of this invention, upon clamping the pipe 4, the position-adjustment mechanism 40 adjusts the position of the pipe 4 such that the perpendicular-line L1 passing through the center of the piezoelectric-device 10 meets the central-axial line L0 of the pipe 4. Thus, the propagation-route of the ultrasonic-waves 'So' being sent and received between the pair of ultrasonic-sensors 11, 12 runs through the central-axial line L0 of the pipe 4. In this case, some space corresponding to the outer-diameter of the pipe 4 can be kept as the ultrasonic-propagation-route of the ultrasonic waves 'So,' thus making it possible to measure the flow-rate of the fluid W1 accurately.

(5) Regarding the sensor-clamp device 2 of the embodiment of this invention, the model number of the pipe 4 and the recommended positions according to the outer-diameters such as M1, M2, M3, M4 or M5 (display part) are provided on the supporting-plate 30. As such, sliding the ultrasonic-sensor 11 to the recommended position M1 to M5, as shown on the display, firmly holds the ultrasonic-sensor 11 easily and surely at the suitable position according to the outer-diameter of the pipe 4, thus making it possible in measuring the flow-rate of the fluid W1 accurately.

(6) Regarding the sensor-clamp device 2 of the embodiment of this invention, the supporting-plate 30 comprises the sliding-mechanism 33 incorporating the guide-trough 34 obliquely extending in the axial-line direction of the pipe 4. As such, the seventh aspect of this invention makes it possible in providing the sliding-mechanism 33 of a comparatively simple design, thus holding down the manufacturing costs of the sensor-clamp device 2.

(7) The sensor-clamp device 2 of the embodiment of this invention comprises a cylindrically shaped acoustic-propagation guide 14 of which the contact-surface 21 (first-surface) at the tip of the sound-propagation guide 14 makes contact with the outer-wall 5 of the pipe 4, thus providing the plate-like piezoelectric-device 10 on the mounting-surface 22 (second-surface) that is slanted with respect to the contact-surface 21. By using the acoustic-propagation guide 14, the ultrasonic-waves 'So' being generated by the piezoelectric-device 10 can be efficiently and securely irradiated into the pipe 4 at the optimum angle. Also, the ultrasonic-sensors 11, 12 are to be attached to the supporting-place 30 by the sensor-holder 15, thus making it easy to assemble the sensor-clamp device 2.

(8) Regarding the clamp-on ultrasonic flow-meter 1 of the embodiment of this invention, even if the pipe 4 being clamped by the sensor-clamp device 2 has various outer-diameters, such diameters of the pipe 4 (4*a*, 4*b*) can be detected automatically by the measurement-control device 3, thus promptly and accurately measuring the flow-rate according to the outer-diameters of the pipe 4.

The Second Embodiment

Figure 11:
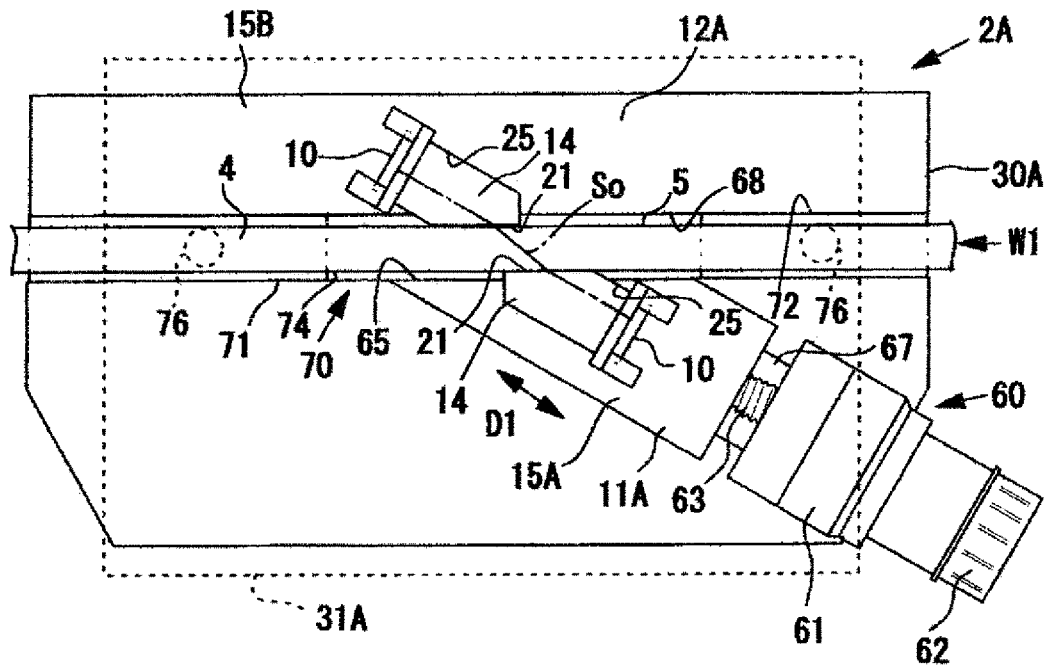
FIG. 11 is the flat view of the sensor-clamp device as the second embodiment.
Figure 12:
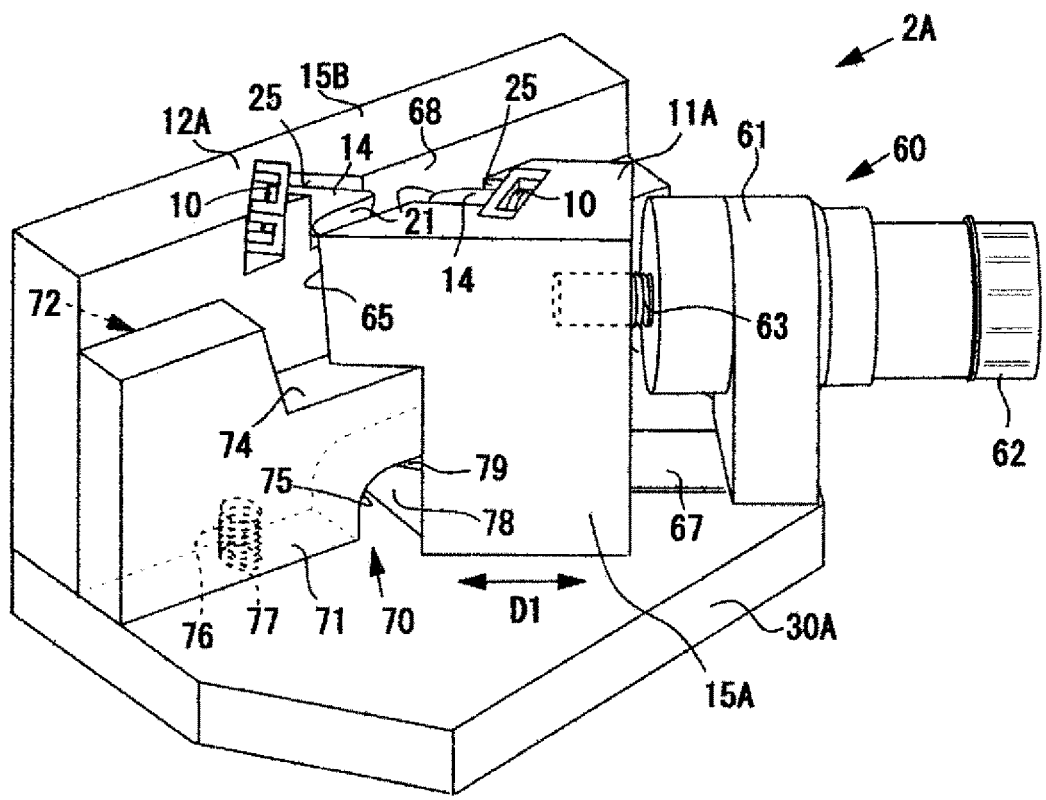
FIG. 12 is the oblique-perspective view of the sensor-clamp device as the second embodiment.

The second embodiment of this invention embodying the clamp-on ultrasonic flow-meter 1 is described in reference to FIGS. 11 and 12. Regarding the clamp-on ultrasonic flow-meter 1 of the embodiment of this invention, the structure of the sensor-clamp device 2A is different from that of the first embodiment. However, the structure of the measurement-control device 3 is the same as that of the first embodiment of this invention. Hereinafter, the structure of the sensor-clamp device 2A is described.

As shown in FIGS. 11 and 12, the linear-slider 60 as the sliding-mechanism for sliding the ultrasonic-sensor 11A obliquely with respect to the pipe 4 is provided on the sensor-clamp device 2A of the embodiment of this invention. The linear-slider 60 comprises the main-fixture 61 to be affixed onto the supporting-plate 30A as the supporting-base; comprises the rotating-operation part 62 provided at the rear of the main-fixture 60; and comprises the sliding-drive 63 provided at the front of the main-fixture 61. The sliding-drive 63 telescopically slides axially from the main-fixture 61 according to the rotational-direction and rotations of the rotating-operation part 62 of the linear-slider 60.

Of the sensor-clamp device 2A, the ultrasonic-sensor 11A is affixed to the sliding-drive 63 of the linear-slider 60. The other ultrasonic-sensor 12A is affixed to the supporting-plate 30A opposite the ultrasonic-sensor 11A. The ultrasonic-sensors 11A, 12A comprise the piezoelectric-device 10, the cylindrically shaped acoustic-propagation guide 14, and the sensor-holder 15A, 15B respectively. The piezoelectric-device 10 and acoustic-propagation guide 14 of ultrasonic-sensors 11A, 12A is of the same shape as that of the first embodiment of this invention except for the sensor-holder 15A, 15B.

The sensor-holder 15A of the ultrasonic-sensor 11A is formed block-shape, and the base of sensor-holder 15A is affixed to the sliding-drive 63 of the linear-slider 60. The surface 65 opposite the ultrasonic-sensor 12A (sensor-holder 15B) is slanted axially to the linear-slider 60. The concave-part 25 in which is stored the acoustic-propagation guide 14 with the attached piezoelectric-device 10 is formed in the upper-central area of the tip of the sensor-holder 15A. The concave-part 25 is provided partially open to the surface 65 of the sensor-holder 15A. As the acoustic-propagation guide 14 is being stored within the concave-part 25 of the sensor-holder 15A, the acoustic-propagation guide 14 is arranged such that the surface 65 of the sensor-holder 15A is in parallel with the contact-surface 21 (first-surface) of the acoustic-propagation guide 14, and the contact-surface 21 is slightly projected beyond the surface 65 of the sensor-holder 15A. On the supporting-plate 30A, a metal-plate 67 is attached to the area onto which the sensor-holder 15A is slid. Such a metal-plate 67 on the supporting-plate 30A reduces friction as the sensor-holder 15A is sliding.

The sensor-holder 15B of the ultrasonic-sensor 12A is formed as a plate in the shape of a rectangle and is affixed upright perpendicular to the upper-surface of the supporting-plate 30A. The concave-part 25 for storing the acoustic-propagation guide 14 with the piezoelectric-device 10 is formed in the central-area of the sensor-holder 15B. The concave-part 25 is provided partially open on the surface 68 opposite the surface 65 of the sensor-holder 15A. As the acoustic-propagation guide 14 is being stored in the concave-part 25 of the sensor-holder 15B, the acoustic-propagation guide 14 is arranged such that the surface 68 of the sensor-holder 15B is in parallel with the contact-surface 21 of the acoustic-propagation guide 14. The contact-surface 21 is slightly projected beyond the surface 68 of the sensor-holder 15B.

The height of sensor-holders 15A, 15B of ultrasonic-sensors 11A, 12A respectively is the same. The pair of sensor-holders 15A, 15B are arranged such that there is a certain amount of space between the surfaces 65, 68 mutually facing each other in parallel, so as to be able to slip the pipe 4 between said surfaces 65, 68 of the sensor-holders 15A, 15B respectively. Of the sensor-clamp device 2A of the second embodiment, as well as that of the first embodiment, the ultrasonic-sensor 11A is slid in the direction D1 in which the ultrasonic-waves 'So' are obliquely flowing into the fluid W1 flowing within the pipe 4.

The vertical-sliding member 71 is arranged between the pair of ultrasonic-sensors 11A, 12A on the supporting-plate 30A of the sensor-clamp device 2A of the embodiment of this invention. The vertical-sliding member 71 is joined to the linear-slider 60 by the sensor-holder 15A. The linear-slider 60 vertically slides the pipe 4 perpendicularly in the horizontal-direction (i.e. the surface-direction of the supporting-plate 30A) in which the ultrasonic-sensor 11A is slid. The vertical-sliding member 71 moves vertically meshing with the interval-adjustment motion of the pair of ultrasonic-sensors 11A, 12A being operated by the linear-slider 60, thus adjusting the position of the pipe 4.

The vertical-sliding member 71 is formed nearly in the shape of a plate and is movable and vertically arranged such that the surface 72 of the vertical-sliding member 71 makes contact with the surface 68 of the sensor-holder 15B and stands perpendicularly to the top-surface of the supporting-plate 30A as well as to that of the sensor-holder 15B. The vertical-sliding member 71 of the embodiment of this invention is made of a resin material, as are the sensor-holders 15A, 15B, and is set below the top-surface of sensor-holder 15A, 15B respectively. The top-surface 72 of the vertical-sliding member 71 is below the top-surface of sensor-holders 15A, 15B respectively. The pipe 4 is arranged to make contact with the top surface of the vertical-sliding member 71.

The first-concave 74 and second-concave 75 are formed of the central top-surface and central bottom-surface respectively of the vertical-sliding member 71. The top-surface of the sensor-holder 15A is projected, and within such projected-part is stored the piezoelectric-device 10 and the acoustic-propagation guide 14. At both ends of the bottom-surface of the vertical-sliding member 71, straddling the second-concave 75, is formed a non-through storage-hole 76. Within each storage-hole 76 is stored a spring 77 of which one end is affixed to the-top-surface (see FIG. 12) of said hole 76, and the other end is affixed to the top-surface of the supporting-plate 30A. Such a provided spring 77 generates tension in the direction in which the vertical-sliding member 71 is pulled along the supporting-plate 30A.

The projection 78, which is slipped into the second-concave 75 of the vertical-sliding member 71 to raise the vertical-sliding member 71, is provided on the lower surface of the sensor-holder 15A that is slid by the linear-slider 60. The projection 78 comprises a slanted-surface 79 descending to the tip of the projection 78. The sensor-holder 15A is slid by the linear-slider 60 as the interval-adjustment work is done in narrowing the interval between the pair of ultrasonic-sensors 11A, 12A. Thus, the projection 78 is slipped into the second-concave 75 of the vertical-sliding member 71, so that the slanted-surface 79 of the projection 78 is within the second-concave 75 of the vertical-sliding member 71 to press the vertical-sliding member 71 upward. Contrarily, the projection 78 is withdrawn from the second-concave 75 of the vertical-sliding member 71 as the sensor-holder 15A is slid by the linear-slider 60 in widening the interval between the ultrasonic-sensors 11A, 12A. At that time, the vertical-sliding member 71 is pulled downward by the springs 77 and descends along the slanted-surface 79 of the projection 78.

As such, the position-adjustment mechanism 70 of the embodiment of this invention consists of the vertical-sliding member 71, the springs 77 and the projection 78 of the sensor-holder 15A. As the interval between the ultrasonic-sensors 11A, 12A is narrowed in sliding the linear-slider 60 to clamp the pipe 4 of a small outer-diameter, the position-adjustment mechanism 70 moves the pipe 4 upward and then adjusts the position of the pipe 4. Contrarily, as the interval between the ultrasonic-sensors 11A, 12A is widened in sliding the linear-slider 60 to clamp the pipe 4 of a large outer-diameter, the position-adjustment mechanism 70 moves the pipe 4 downward and then adjusts the position of the pipe 4. Providing such a position-adjustment mechanism 70 makes it possible in adjusting the position of the pipe 4 such that the line L1 passing through the center of the piezoelectric-device 10 of the pair of ultrasonic-sensors 11A, 12A meets the central-axial line L0 of the pipe 4.

As well as the aforementioned sensor-clamp device 2 of the first embodiment of this invention, the sensor-clamp device 2A of the second embodiment of this invention comprises a cross-sectional U-shaped cover 31A. The pressing-member (e.g. an elastic body such as a sponge or the like) is arranged above the pipe 4 and against the inner-side of the cover 31A. With the U-shaped cover 31A attached, the pipe 4 is pressed downward from above by the pressing-member. Thus, in being slipped between the pressing-member and the vertical-sliding member 71, the pipe 4 is pressed upward and downward and thus firmly affixed so that it cannot come off vertically.

The effect of the sensor-clamp device 2A of the second embodiment of this invention is similar to that of the sensor-clamp device 2 of the first embodiment of this invention. In conjunction with the interval-adjustment work, the position-adjustment mechanism 70 can be moved vertically by the linear-slider 60 as the sliding-mechanism between the pair of ultrasonic-sensors 11A, 12A is adjusting the position of the pipe 4. As such, compared to the case of which the interval-adjustment by the sliding-mechanism 60 and the position-adjustment are done separately, the setting of the sensor-clamp device 2A (i.e. the clamping of the pipe 4) of this invention can be done fairly simply and quickly.

Each embodiment below of this invention can be modified.

As describe above in the first embodiment of this invention, the sliding-mechanism 33 comprises the guide-trough 34 extending obliquely in the axial-line direction of the pipe 4 on the supporting-plate 30 and obliquely slides the other ultrasonic-sensor 11. Yet, the sliding-mechanism 33 is not limited to doing just that. If the type of fluid W1 flowing within the pipe 4 is varied, and the sonic-speed of the fluid W1 is changed, then the direction D1 in which the ultrasonic-waves 'So' forward into the fluid W1 will be changed. In that case it is possible to make the sliding-mechanism 33 such that the number of guide-troughs 34 are increased in an oblique direction of different angles with respect to the axial-line direction of the pipe 4 on the supporting-plate 30, so as to slide the ultrasonic-sensors 11, 12 in such various oblique directions along to the guide-troughs 34. Of the sliding-mechanism 33, each guide-trough 34 is formed at a suitable pitch-angle based on the sonic-speed of the various types of fluid W1 that are presumably being used, thus being able to set the direction in which the ultrasonic-sensors 11, 12 are to be slid. In that case it is possible to form each guide-trough 34 of the sliding-mechanism 33 so as to be able to slide one ultrasonic-sensor 11 in various oblique directions or to be able to slide the pair of ultrasonic-sensors 11, 12 in various oblique directions. Moreover, it is possible to form a V-shaped guide-trough or the like of which one end of the two linear guide-troughs 34 are connected so as to be slid in different directions.

The guide-trough 34 of the sliding-mechanism 33 is formed and the linear-slider 60 is arranged in each embodiment of the above sensor-clamp devices 2, 2A of this invention to let the ultrasonic-sensors 11, 11A be slid in the direction D1 in which the ultrasonic-waves 'So' forward obliquely into the fluid W. Yet, such guide-trough 34 and linear-slider 60 are not limited in doing just that function. The sliding-mechanism 33 or the linear-slider 60 can also let the ultrasonic-sensors 11, 11A be slid in the direction in which the ultrasonic-waves 'So' that had been irradiating into the pipe 4 now to forward obliquely into the wall of the pipe 4.

Figure 13:
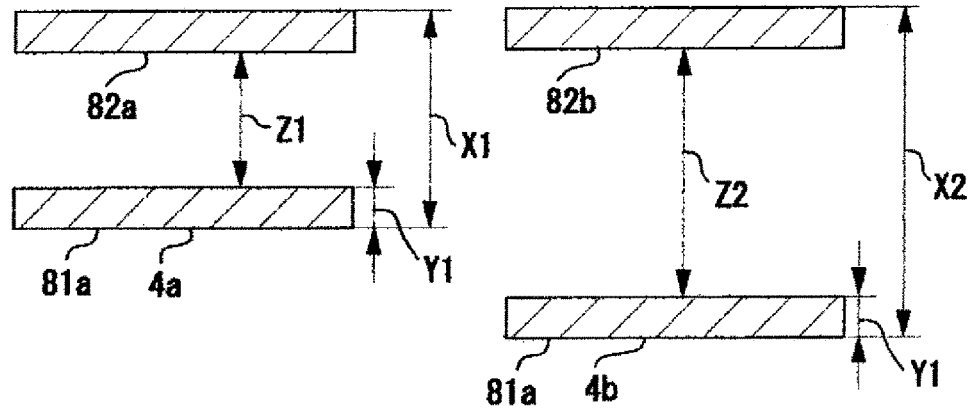
FIG. 13 is the cross-sectional view of a pipe of which the thickness of the wall is the same but that the inner and outer diameters are different.
Figure 14:
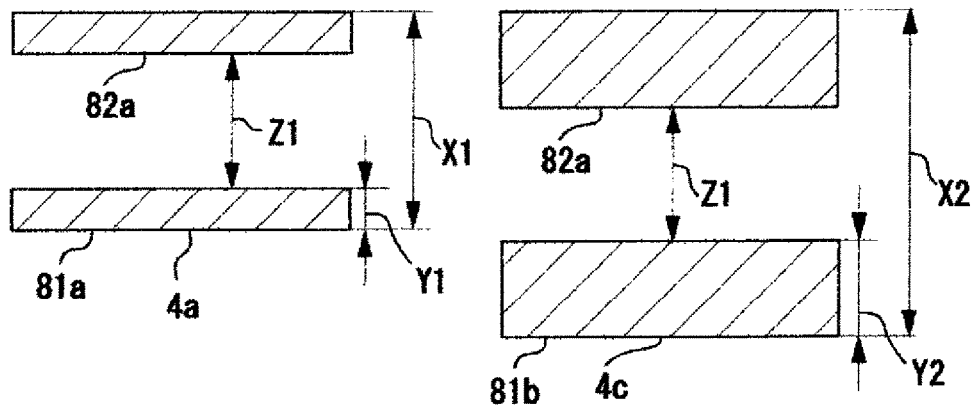
FIG. 14 is the cross-sectional view of a pipe of which the thickness of the wall is different and that the outer-diameter is different.

Regarding the above first embodiment, the pitch-angle $\theta_0$ of the guide-trough 34 has been conventionally calculated assuming that the sonic-speed within the wall of the pipe 4 is equal to the sonic-speed $c_2$ within the fluid W1. However, the sonic-speed within the wall of the pipe 4 could be different than the sonic speed $c_2$ within the fluid W1. As shown in FIG. 13, there are other types of the pipe 4 of different outer-diameters X1, X2 such as the pipes 4a, 4b of the same thickness Y1 as the pipe-wall 81a but of different widths Z1, Z2 (i.e. the inner-diameters of the pipe 4a, 4b) of the flow-path 82a, 82b or of the pipe 4a, 4c as shown in FIG. 14 that have the same width Z1 (i.e. the inner-diameter of the pipes 4a, 4c) of the flow-path 82a but are of a different thickness Y1, Y2 of the pipe-wall 81a, 81b.

Figure 15:
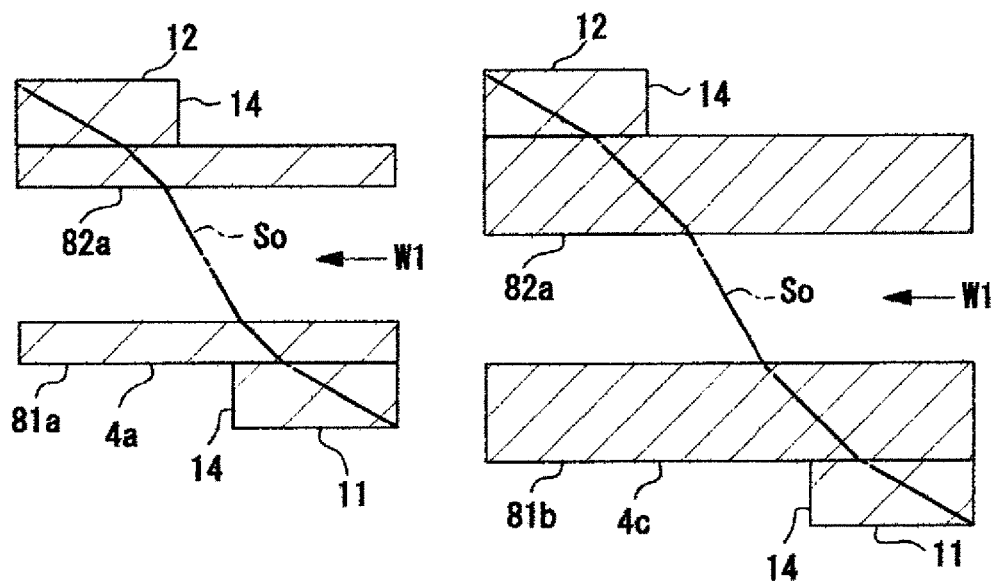
FIG. 15 is the explanatory diagram showing the ultrasonic-propagation route within a pipe of different outer-diameters.
Figure 16:
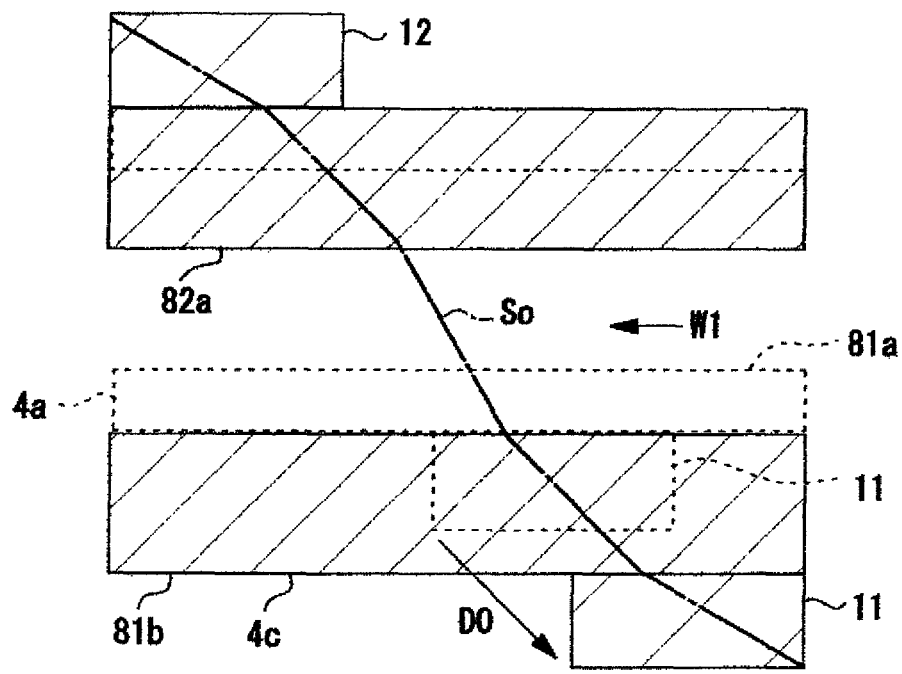
FIG. 16 is the explanatory diagram showing the sliding-direction of the ultrasonic-sensors in the case in which the pipe becomes thicker.

Assuming that the sonic-speed within the acoustic-propagation guide 14 and in the fluid W1 and in the walls 81a, 81b of the pipe 4a, 4c is $c_1$, $c_2$ and $c_3$ respectively, thus making the mutual relationship $c_1 > c_3 > c_2$, and, with the pair of ultrasonic-sensors 11, 12 clamping the pipes 4a, 4c of the same width Z1 (i.e. of the same inner-diameter) of the flow-path 82a but that the walls 81a, 81b are of different thicknesses Y1, Y2 respectively, as shown in FIG. 15, the propagation-route of such ultrasonic-waves 'So,' whereof said propagation-route of the ultrasonic-waves 'So' within the pipes 4a, 4c are of different outer-diameters, the propagation-route of the ultrasonic-waves 'So' within the walls 81a, 81b would then be changed. In that case, as shown in FIG. 16, the reception-sensitivity of the ultrasonic-waves 'So' would be kept by sliding one ultrasonic-sensor 11 obliquely in the direction D0 in which the ultrasonic-waves 'So' are forwarding obliquely within the walls 81a, 81b.

Figure 17:
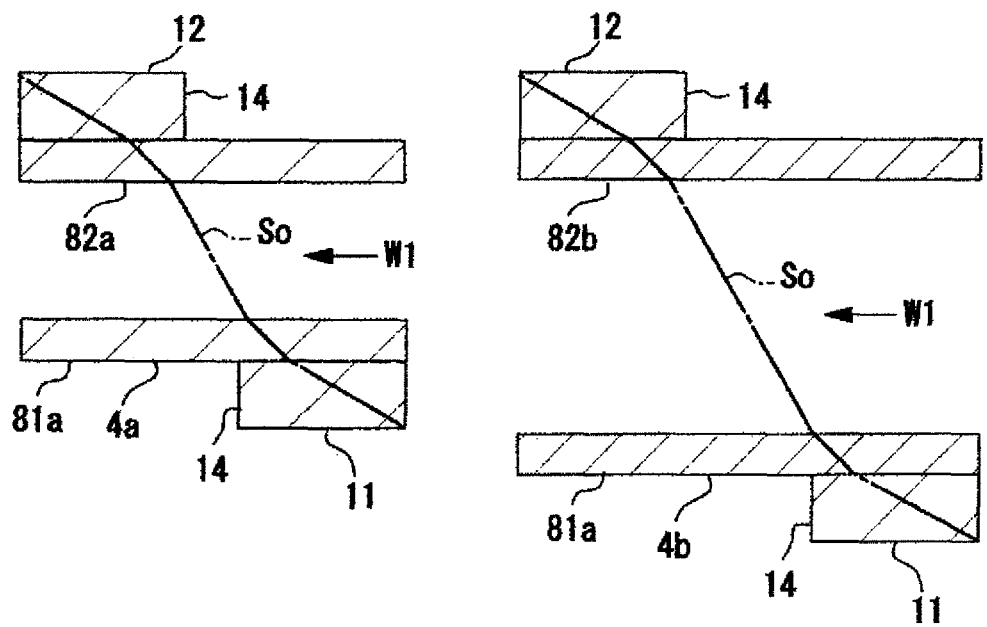
FIG. 17 is the explanatory diagram showing the ultrasonic-propagation route within a pipe of different outer-diameters.
Figure 18:
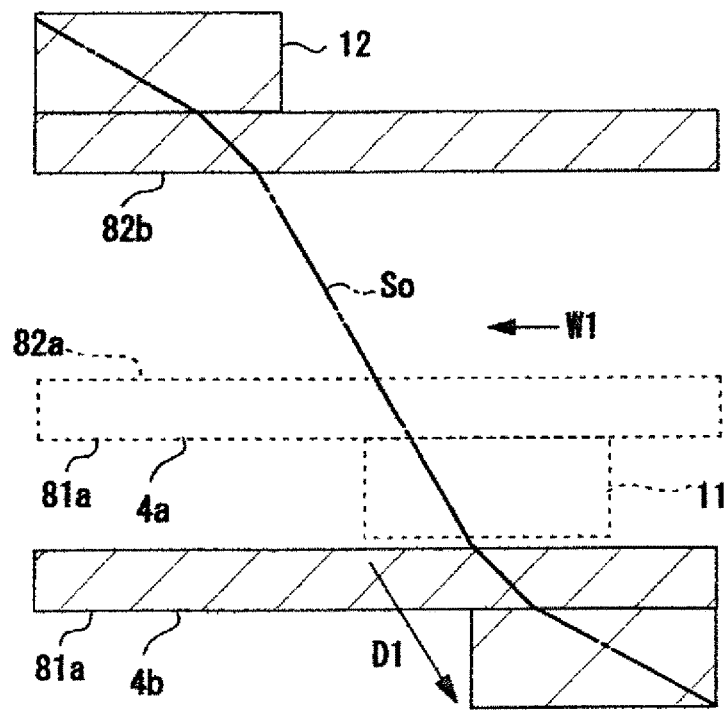
FIG. 18 is the explanatory diagram showing the sliding-direction of the ultrasonic-sensors in the case in which the pipe becomes thicker.

Assuming that the wall 81a of the pipes 4a, 4b is of the same thickness Y1 but that said pipes are of different (inner-diameter) widths Z1, Z2 in forming the respective flow-paths 82a, 82b, with the pipes 4a, 4b being clamped by the pair of ultrasonic sensors 11, 12, the ultrasonic-waves 'So' propagation route, as shown in FIG. 17, whereof such propagation route of the ultrasonic-waves 'So' that forward (in the fluid W1) within the wall flow-paths 82a, 82b respectively would be changed. In this case, as shown in FIG. 18, the reception-sensitivity of the ultrasonic-waves 'So' is maintained by sliding one ultrasonic sensor 11 obliquely in the direction D1 in which the ultrasonic-waves 'So' obliquely are forwarding into the fluid W1.

Figure 19:
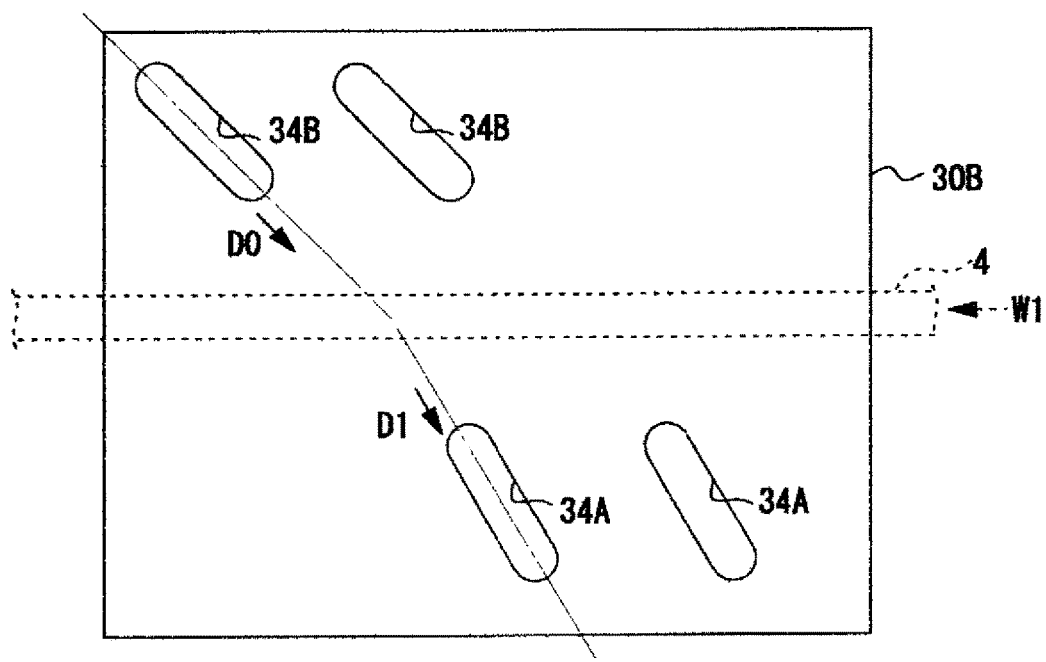
FIG. 19 is the flat view of the clamped plate of which the guide-trough is formed as another embodiment.

As shown in FIG. 19, the supporting-plate 30B is formed such that the guide-trough 34A for sliding one ultrasonic-sensor 11 is set in the direction D1 in which the ultrasonic-waves 'So' obliquely forward into the fluid W1, and that the guide-trough 34B for sliding the other ultrasonic sensor 12 is set in the direction D0 in which the ultrasonic-waves 'So' obliquely forward within the walls 81a, 81b. As such, the two guide-troughs 34A, 34B of different pitch-angles are provided, thus making it possible in clamping the pipes 4 (4a to 4c) by the pair of ultrasonic-sensors 11, 12 at each appropriate position according to the different outer-diameters of the pipes 4 (4a to 4c).

Figure 20:
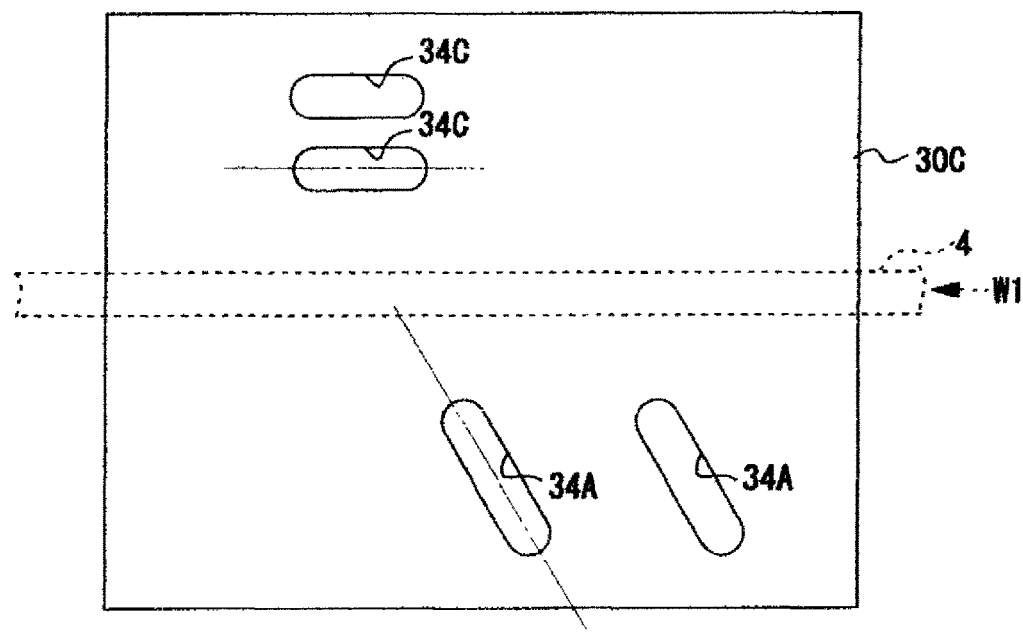
FIG. 20 is another flat view of the clamped plate of which the guide-trough is formed as another embodiment.

As described in each embodiment of this invention, the pipe 4 (4a to 4c) is a transfusion-pipe made of an elastic resin-material, but it is not limited to just that material. It is also possible to use a metallic pipe. When comparing the pipes 4 of the same outer-diameter and of the same thickness as the wall 81a but of a different material than that of the wall 81a, i.e. of resin or of metal, the sonic speed within the wall 81a is greatly different. Thus, in clamping by the pair of ultrasonic-sensors 11, 12 the pipe 4 of the same outer-diameter and of the same thickness as the wall 81a but of a different material than that of the wall 81a, the pitch-angle of the ultrasonic-waves 'So' obliquely forwarding within the wall 81a is changed. Thus, the appropriate position at which the ultrasonic-waves 'So' are sent and received moves in the axial-line direction of the pipe. Therefore, in changing the material of the pipe 4, as shown in FIG. 20, it is possible to provide on the supporting-plate 30 the first guide-trough 34A (the first sliding-mechanism) for sliding one ultrasonic-sensor 11 obliquely with respect to the pipe 4 and the second guide-trough 34C (the second sliding-mechanism) for sliding the other ultrasonic-sensor 12 in parallel with the pipe 4. If the outer-diameter of the pipe 4 is changed, then the pipe 4 is clamped by obliquely sliding one ultrasonic-sensor 11 along the first guide-trough 34A and in parallel with the pipe 4. Also if the material of the pipe 4 is changed, then the pipe 4 is clamped by sliding the other ultrasonic-sensor 12 along the second guide-trough 34C and in parallel with the pipe 4. Such a configuration of the sensor-clamp device allows for the pair of ultrasonic-sensors 11, 12 to clamp the pipe 4 at the appropriate position according to the outer-diameters of the pipe 4.

Figure 21:
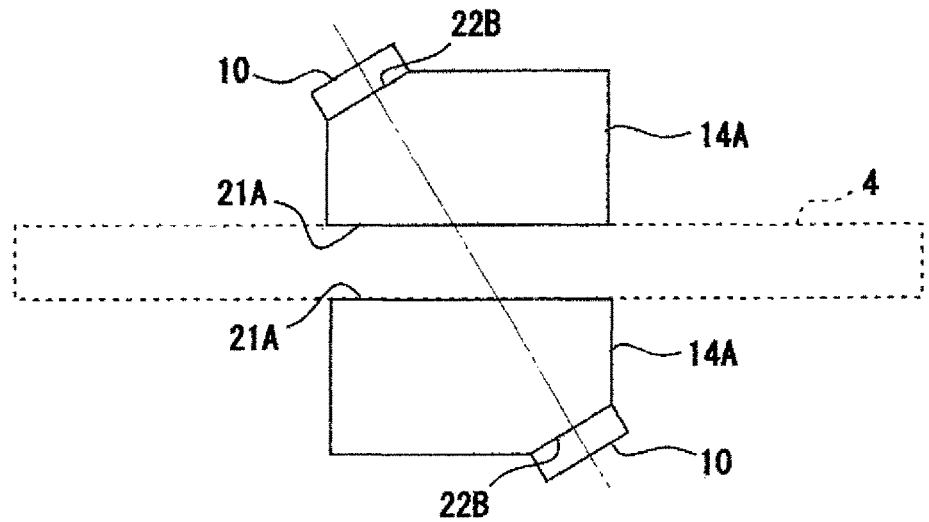
FIG. 21 is the flat view of the acoustic-propagation guide as another embodiment.
Figure 22:
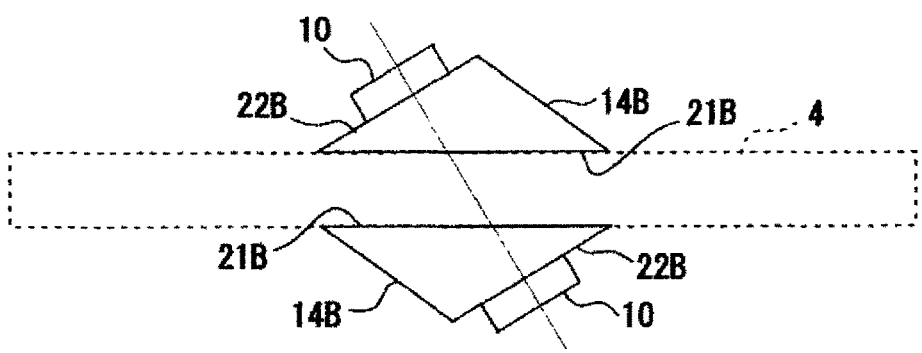
FIG. 22 is another flat view of the acoustic-propagation guide as another embodiment.
Figure 23:
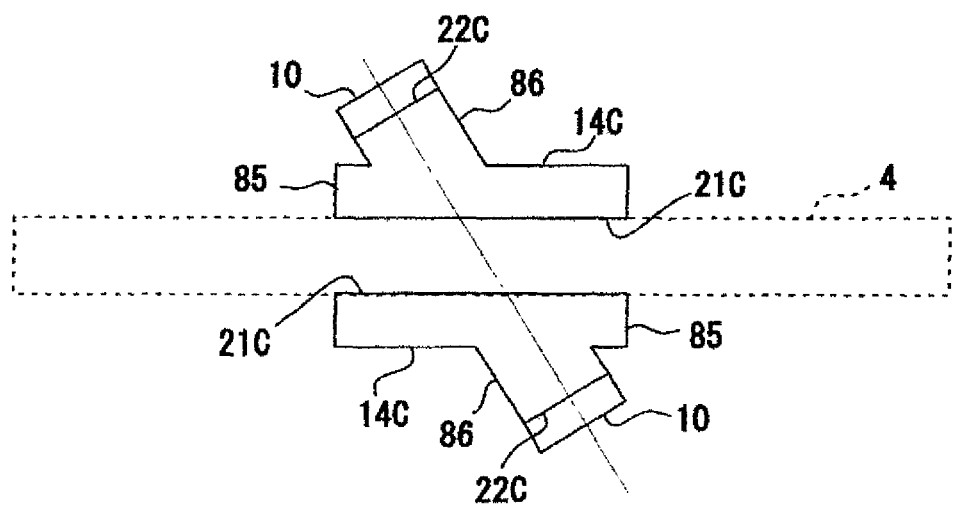
FIG. 23 is still another flat view of the acoustic-propagation guide as another embodiment.

As for the sensor-clamp devices 2, 2A of each embodiment of this invention, the acoustic-propagation guide 14 of the ultrasonic-sensor 11, 11A, 12, 12A is shaped like a disk. However, it is possible to deform said acoustic-propagation guide 14 if it comprises the contacting-surface 21 (first-surface) in contact with the outer-wall 5 of the pipe 4 and the mounting-surface 22 (second-surface) that is slanted toward the contact-surface 21, with the piezoelectric-device 10 being provided on the contact-surface 21. Examples of such deformation of the acoustic-propagation guide 14A, 14B and 14C are shown in FIGS. 21 to 23. The acoustic-propagation guide 14A, as shown in FIG. 21, is shaped like a square, and thereof one corner is chamfered, and such a chamfered-surface on the acoustic-propagation guide 14A is the mounting-surface 22B on which the piezoelectric-device 10 is to be placed. The opposite side of the chamfered-mounting surface 22B is the contacting-surface 21A on which the pipe 4 is to make contact. The acoustic-propagation guide 14B, as shown in FIG. 22, is shaped like a triangle thereof one surface is the mounting-surface 22B on which the piezoelectric-device 10 is to be mounted and thereof the other surface is the contacting-surface 21B on which the pipe 4 is to make contact. The acoustic-propagation guide 14C, as shown in FIG. 23, is of a projected shape, and thereof said guide the projection 86 is provided obliquely from the flat plate-member 85, and the end of the projection 86 is the mounting-surface 22C on which the piezoelectric-device 10 is to be mounted. Opposite the surface of the flat plate-member 85, from which projects the projection 86, is the contact-surface 21C on which the pipe 4 makes contact. Such a configuration of the ultrasonic-sensors in using each of acoustic-propagation guide 14A to 14C makes it possible in irradiating the ultrasonic-waves 'So' obliquely into the pipe 4.

As for the sensor-clamp device 2 of the embodiment of this invention, the position-adjustment mechanism 40 is made by the use of a sponge as the pressing-member 41, 42 in pressing and supporting the pipe 4 vertically. However, rather than using a sponge, it is possible to use a spring or the like. It is also possible to provide a clamp-member similar in shape to that of a crab-claw for clamping the pipe 4 at a different position than where the pair of ultrasonic-sensors 11, 12 clamp the pipe 4 and then adjusts it at that position.

As for the sensor-clamp device 2, 2A of each embodiment of this invention, the supporting-plate 30, 30A to 30C is used as the supporting-base. However, a frame-body, or many bars or the like, can be used also if such things can support the pair of ultrasonic-sensors 11, 11A, 12, 12A. If the supporting-base is made of many bars, some of the bars can also be used as the sliding-mechanism 33.

The clamp-on ultrasonic flow-meter of each embodiment of this invention is used in measuring the flow-rate of a blood-infusion at a medical front. However, such a flow-meter can also be used in measuring the flow-rate of any liquid within pipes in a factory.

The clamp-on ultrasonic flow-meter 1 of each embodiment of this invention has the function of which the measurement-control device 3 automatically detects the size of the outer-diameter of the pipe 4, but it is not limited to that function. It is also possible for an operator to set the types and sizes of outer-diameters or the like of the pipe 4 manually by operating the input-device 52 of the measurement-control device 3 and then to calculate the flow-rate of the fluid according to such set information.

Besides the technical ideas described in this invention, other technical ideas to be understood are described hereinafter.

(1) A sensor-clamp device, according to the first aspect of this invention, characterized in that the ultrasonic-sensor is slid in the direction in which the ultrasonic-waves are irradiating into the pipe and obliquely forwarding into the walls of the pipe.

(2) A sensor-clamp device, according to the second aspect of this invention, characterized in that the sliding-mechanism slides the ultrasonic-sensor at an angle of ±10° with respect to the angular-direction in which the ultrasonic-waves are forwarding into the fluid.

(3) A sensor-clamp device, according to the fourth or fifth aspect of this invention, characterized in that the sliding-mechanism comprises a linear-slider that retains one of the pair of ultrasonic-sensors and slides it obliquely with respect to the pipe, with the position-adjustment mechanism being connected to the linear-slider for adjusting the central position of the pipe in conjunction with the sliding-motion.

(4) A sensor-clamp device, according to the above technical idea (3), characterized in that as the interval between each ultrasonic-sensor is narrowed in sliding the linear-slider to clamp the pipe of a small outer-diameter, the position-adjustment mechanism moves the pipe upward and adjusts the position of the pipe, and that contrarily as the interval between each ultrasonic-sensor is widened in sliding the linear-slider to clamp the pipe of a large outer-diameter, the position-adjustment mechanism moves the pipe downward and adjusts the position of the pipe.

(5) A sensor-clamp device, according to the fourth or fifth aspect of this invention, characterized in that the position-adjustment mechanism comprises a pressing-member for adjusting the position of the pipe 4 by supporting the pipe 4 from both sides in the orthogonal-direction in which the pair of ultrasonic-sensors are placed face-to-face.

(6) A sensor-clamp device, according to the fourth or fifth aspect of this invention, characterized in that the position-adjustment mechanism comprises a clamping-member for tucking the pipe into a position other than that whereat the pipe is to be clamped by the pair of ultrasonic-sensors and said position of the pipe is to be adjusted.

(7) A sensor-clamp device, according to the fourth or fifth aspect of this invention, characterized in that the supporting-base is a supporting-plate and that the sliding-mechanism slides the ultrasonic-sensor in the surface-direction of said supporting-plate and that the position-adjustment mechanism vertically moves the pipe in the orthogonal-direction of the surface-direction.

(8) A sensor-clamp device, according to the seventh aspect of this invention, characterized in that the sliding-mechanism comprises a number of guide-troughs extending in oblique directions at various angles with respect to the axial-line direction of the pipe.

(9) A sensor-clamp device, according to the seventh aspect of this invention, characterized in that the supporting-base comprises the first sliding-mechanism for sliding one of the ultrasonic-sensors obliquely with respect to the pipe and comprises the second sliding-mechanism for sliding the other ultrasonic-sensor in parallel with the pipe.

(10) A sensor-clamp device, according to the seventh aspect of this invention, characterized in that the sliding-mechanism comprises an affixing-bolt for affixing the ultrasonic-sensor to be engaged in the guide-trough.

(11) A sensor-clamp device, according to the eighth aspect of this invention, characterized in that the piezoelectric-device is formed in the shape of a disk and that the acoustic-propagation guide is cylindrically formed and that the first and second surfaces are provided at the tip and base respectively of the acoustic-propagation guide.

(12) A sensor-clamp device, according to any one of the first to eighth aspects of this invention, characterized in that the sliding-direction of the ultrasonic-sensor is set based on the sonic-speed within the fluid.

(13) A sensor-clamp device, according to any one of the first to eighth aspects of this invention, characterized in that the pipe is a tube made of an elastic material.

DESCRIPTION OF THE REFERENCE SIGNS

1: Clamp-on ultrasonic flow-meter
2, 2A: Sensor-clamp device
3: Measurement-control device as the arithmetic-processing means for calculating the flow-rate of the fluid
4, 4a, 4b, 4c: Pipe
5: Outer wall
10: Piezoelectric-device as the ultrasonic-transducer
11, 11A, 12, 12A: Ultrasonic-sensor
14, 14A, 14B, 14C: Acoustic-propagation guide
15, 15A, 15B: Sensor-holder
21, 21A, 21B, 21C: Contact-surface as the first-surface
22, 22A, 22B, 22C: Mounting-surface as the second-surface
30, 30A, 30B, 30C: Supporting-plate as the supporting-base
33: Sliding-mechanism
34, 34A, 34B: Guide-trough comprising the sliding-mechanism
35: Affixing-bolt of the sliding-mechanism
40, 70: Position-adjustment mechanism
41, 42: Pressing-member of the position-adjustment mechanism
60: Linear-slider as the sliding-mechanism
71: Vertical sliding-member as the position-adjustment mechanism
77: Spring of the position-adjustment mechanism
78: Projection of the position-adjustment mechanism
D1: Direction of the ultrasonic-waves flowing into the fluid
L0: Central-axial line
L1: Line
54
So: Ultrasonic-waves
W1: Fluid
X1, X2: Outer-diameter
θ1: Pitch-angle of the ultrasonic-waves forwarding into the fluid
θ2: Pitch-angle of the ultrasonic-waves irradiating into the pipe

The invention claimed is:
1. A sensor-clamp device comprising:
a pair of ultrasonic-sensors incorporating an ultrasonic-transducer for sending and receiving ultrasonic-waves; the pair of ultrasonic-sensors clamped in close contact to an outer-wall of a pipe in which fluid is flowing, wherein the pair of ultrasonic-sensors are offset in an axial-direction of the pipe and placed in an opposing manner so that the ultrasonic-waves are obliquely irradiated into the pipe; wherein ultrasonic-waves are sent and received mutually between the pair of ultrasonic-sensors for calculating by arithmetic processing a flow-rate of the fluid flowing within the pipe according to the ultrasonic-propagation time-lag; and wherein each pair of the ultrasonic-sensors further comprises a disc-shaped piezoelectric-device a supporting base, wherein the supporting-base has a sliding-mechanism that can slide at least one of the pair of ultrasonic-sensors obliquely with respect to an axial-direction of the pipe, thus making it possible to clamp a pipe of various outer-diameters, an acoustic-propagation guide for each ultrasonic sensor, each acoustic-propagation guide with a first-surface thereof contacting an outer-wall of a straight-shaped part of the pipe and a second-surface of the acoustic-propagation guide contacting each piezoelectric-device provided thereon, the second surface being slanted with respect to the first surface for propagating the ultrasonic waves between the piezoelectric-device and the pipe; and a sensor-holder for holding each of the acoustic-propagation guides and for attaching the acoustic-propagation guides to the supporting-base, and further wherein on a condition that a crossing-angle between a normal-vector of the piezoelectric-device and a normal-vector of the flow-path within the pipe is specified as $\theta 3$ [rad], a sonic-speed to propagate the sound-propagation guide is specified as $c_1$, and a sonic-speed within the fluid is specified as $c_2$, an incident-angle $\theta 4$ [rad] between a normal vector of the flow-path within the pipe and the sliding direction in which the ultrasonic-waves are forwarding in the fluid of the pipe satisfies a relationship, as shown in Formula 1;

$$\theta_4 = \arcsin\left(\frac{\sin\theta_3}{c_1} \times c_2\right). \quad \text{Formula 1}$$

2. A sensor-clamp device, according to claim 1, wherein the ultrasonic-sensors are slid in a direction in which the ultrasonic-waves are irradiating into the pipe and obliquely forwarding into the fluid flowing within the pipe.

3. A sensor-clamp device, according to claim 2, wherein a pitch-angle of the ultrasonic-waves forwarding into the fluid flowing within the pipe with respect to an axial-line direction of the pipe is set to be greater than a pitch-angle of the ultrasonic-waves irradiating into the pipe with respect to the axial-line direction of the pipe.

4. A sensor-clamp device, according to claim 1, wherein the supporting-base comprises a position-adjustment mechanism for adjusting the position of the pipe such that a perpendicular-line passing through a center each ultrasonic-transducer of the pair of ultrasonic-sensors meets a central-axial line of the pipe.

5. A sensor-clamp device, according to claim 4, wherein the position-adjustment mechanism moves up and down between the pair of ultrasonic-sensors due to the sliding-mechanism, thus adjusting the position of the pipe.

6. A sensor-clamp device, according to claim 1, wherein a position of the ultrasonic-sensors as the ultrasonic sensors are being slid and affixed by the sliding-mechanism is defined according to each outer-diameter of the pipe, with a display being provided on the supporting-base of the sensor-clamp device for simultaneously showing the position.

7. A sensor-clamp device, according to claim 1, wherein the sliding-mechanism comprises a guide-trough that obliquely extends on the supporting-base in the direction of the axial-direction of the pipe.

8. A clamp-on ultrasonic flow-meter comprising a sensor-clamp device, according to claim 1, and a controller for calculating the flow-rate of the fluid according to the ultrasonic-propagation time lag.

9. A clamp-on ultrasonic flow-meter, according to claim 8, wherein the controller automatically detects the size of the outer-diameter of the pipe according to the ultrasonic-propagation time, thus arithmetically calculating the flow-rate according to the outer-diameter of the pipe.

\* \* \* \* \*